(12) United States Patent
An et al.

(10) Patent No.: US 10,688,304 B2
(45) Date of Patent: Jun. 23, 2020

(54) METHOD AND SYSTEM FOR UTILIZING AN ATRIAL CONTRACTION TIMING FIDUCIAL IN A LEADLESS CARDIAC PACEMAKER SYSTEM

(71) Applicant: CARDIAC PACEMAKERS, INC., St. Paul, MN (US)

(72) Inventors: Qi An, Blaine, MN (US); Pramodsingh Hirasingh Thakur, Woodbury, MN (US); Yinghong Yu, Shoreview, MN (US); Michael J. Kane, St. Paul, MN (US); Jeffrey E. Stahmann, Ramsey, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 260 days.

(21) Appl. No.: 15/625,655

(22) Filed: Jun. 16, 2017

(65) Prior Publication Data
US 2018/0021581 A1    Jan. 25, 2018

Related U.S. Application Data

(60) Provisional application No. 62/364,624, filed on Jul. 20, 2016.

(51) Int. Cl.
*A61N 1/365*    (2006.01)
*A61N 1/375*    (2006.01)
(Continued)

(52) U.S. Cl.
CPC ....... *A61N 1/36585* (2013.01); *A61N 1/3756* (2013.01); *A61N 1/37205* (2013.01);
(Continued)

(58) Field of Classification Search
CPC .............. A61N 1/3756; A61N 1/37205; A61N 1/36578; A61N 1/36564; A61N 1/36585
See application file for complete search history.

(56) References Cited

U.S. PATENT DOCUMENTS

| 3,835,864 A | 9/1974 | Rasor et al. |
| 3,943,936 A | 3/1976 | Rasor et al. |
(Continued)

FOREIGN PATENT DOCUMENTS

| AU | 2008279789 B2 | 10/2011 |
| AU | 2008329620 B2 | 5/2014 |
(Continued)

OTHER PUBLICATIONS

US 8,886,318 B2, 11/2014, Jacobson et al. (withdrawn)
(Continued)

*Primary Examiner* — George R Evanisko
(74) *Attorney, Agent, or Firm* — Seager, Tufte & Wickhem LLP

(57) ABSTRACT

A leadless cardiac pacemaker (LCP) is configured to sense cardiac activity and to pace a patient's heart and is disposable within a ventricle of the patient's heart. The LCP may include a housing, a first electrode and a second electrode that are secured relative to the housing and are spaced apart. A controller is disposed within the housing and is operably coupled to the first electrode and the second electrode such that the controller is capable of receiving, via the first electrode and the second electrode, electrical cardiac signals of the heart. The LCP may include a pressure sensor and/or an accelerometer. The controller may determine an atrial contraction timing fiducial based at least in part upon two or more of a signal from the pressure sensor, a signal from the accelerometer representing, and an electrical cardiac signal.

16 Claims, 16 Drawing Sheets

(51) Int. Cl.
  *A61N 1/372* (2006.01)
  *A61N 1/39* (2006.01)
  *A61B 7/04* (2006.01)

(52) U.S. Cl.
  CPC ....... *A61N 1/37288* (2013.01); *A61N 1/3925* (2013.01); *A61N 1/3962* (2013.01); *A61N 1/3987* (2013.01); *A61B 7/04* (2013.01); *A61N 1/36564* (2013.01); *A61N 1/36578* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Kludziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole |
| 4,905,706 A * | 3/1990 | Duff ............... A61B 5/0436 600/508 |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | DePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | DePinto |

(56) References Cited

U.S. PATENT DOCUMENTS

| | | |
|---|---|---|
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |

(56) References Cited

U.S. PATENT DOCUMENTS

| | | |
|---|---|---|
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |

(56) References Cited

U.S. PATENT DOCUMENTS

| | | |
|---|---|---|
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |

(56) References Cited

U.S. PATENT DOCUMENTS

| | | |
|---|---|---|
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |

(56) References Cited

U.S. PATENT DOCUMENTS

| | | |
|---|---|---|
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0049977 A1* | 3/2007 | Von Arx .......... A61B 7/023 607/9 |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239218 A1* | 10/2007 | Carlson .......... A61B 5/02028 607/18 |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228094 A1* | 9/2008 | Audet .......... A61B 5/0006 600/513 |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1* | 4/2009 | Brockway .......... A61N 1/0587 607/14 |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |

(56) References Cited

U.S. PATENT DOCUMENTS

| | | |
|---|---|---|
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160787 A1 | 6/2011 | Greenhut et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296228 A1* | 11/2012 | Zhang .............. A61B 5/0006 600/513 |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1* | 12/2013 | Karst ............... A61N 1/36592 607/25 |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0121719 A1* | 5/2014 | Bonner ............... A61N 1/3756 607/18 |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |

(56) References Cited

U.S. PATENT DOCUMENTS

| | | |
|---|---|---|
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bomzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0300704 A1 | 10/2014 | Suwito et al. |
| 2014/0303704 A1 | 10/2014 | Suwito et al. |
| 2014/0309706 A1 | 10/2014 | Jacobson |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0067486 A1* | 3/2016 | Brown ............... A61B 5/0452 607/17 |
| 2016/0067490 A1 | 3/2016 | Carney et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129262 A1 | 5/2016 | Sheldon et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368347 A1* | 12/2017 | Muessig ............... A61N 1/3622 |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |

(56) References Cited

FOREIGN PATENT DOCUMENTS

OTHER PUBLICATIONS

International Search Report and Written Opinion dated Oct. 5, 2017 for International Application No. PCT/US2017/037961.
"Instructions for Use System 1, Leadless Cardiac Pacemaker (LCP) and Delivery Catheter," Nanostim Leadless Pacemakers, pp. 1-28, 2013.
Asirvatham et al., "Intramyocardial Pacing and Sensing for the Enhancement of Cardiac Stimulation and Sensing Specificity," PACE, vol. 30, pp. 748-754, Jun. 2007.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Henz et al., "Synchronous Ventricular Pacing without Crossing the Tricuspid Valve or Entering the Coronary Sinus-Preliminary Results," Journal of Cardiovascular Electrophysiology, vol. 20(12):1391-1397, Dec. 2009.doi: 10.1111/j.1540-8167.2009.01556.x.
Hyde et al., "Beneficial Effect on Cardiac Resynchronization From Left Ventricular Endocardial Pacing Is Mediated by Early Access to High Conduction Velocity Tissue Electrophysiological Simulation Study, Circ Arrhythm Electrophysiol, 8, 1164-1172, 2015, DOI: 10.1161/CIRCEP.115.002677.
Notification of Transmittal of the International Search Report and the Written Opinion of the International Searching Authority, or the Declaration, dated Jan. 29, 2016, 15 pages.
Seyedi et al., "A Survey on Intrabody Communications for Body Area Network Application," IEEE Transactions on Biomedical Engineering,vol. 60(8): 2067-2079, 2013.
Spickler et al., "Totally Self-Contained Intracardiac Pacemaker," Journal of Electrocardiology, vol. 3(3&4): 324-331, 1970.
Wegmüller, "Intra-Body Communication for Biomedical Sensor Networks," Diss. ETH, No. 17323, 1-173, 2007.

\* cited by examiner

METHOD AND SYSTEM FOR UTILIZING AN ATRIAL CONTRACTION TIMING FIDUCIAL IN A LEADLESS CARDIAC PACEMAKER SYSTEM

CROSS REFERENCE TO RELATED APPLICATIONS

This application claims the benefit of U.S. Provisional Patent Application Ser. No. 62/364,624 filed on Jul. 20, 2016, the disclosure of which is incorporated herein by reference.

TECHNICAL FIELD

The present disclosure generally relates to implantable medical devices, and more particularly, to systems that use a leadless cardiac pacemaker for monitoring, pacing and/or defibrillating a patient's heart

BACKGROUND

Implantable medical devices are commonly used today to monitor a patient and/or deliver therapy to a patient. For example and in some instances, pacing devices are used to treat patients suffering from various heart conditions that may result in a reduced ability of the heart to deliver sufficient amounts of blood to a patient's body. Such heart conditions may lead to slow, rapid, irregular, and/or inefficient heart contractions. To help alleviate some of these conditions, various medical devices (e.g., pacemakers, defibrillators, etc.) can be implanted in a patient's body. Such devices may monitor and in some cases provide electrical stimulation (e.g. pacing, defibrillation, etc.) to the heart to help the heart operate in a more normal, efficient and/or safe manner. In some cases, it is beneficial to sense and/or pace two or more chambers of the heart, such as to provide cardiac resynchronization therapy (CRT).

SUMMARY

This disclosure generally relates to implantable medical devices, and more particularly, to systems that use a leadless cardiac pacemaker for monitoring, pacing and/or defibrillating a patient's heart. In an example of the disclosure, a leadless cardiac pacemaker (LCP) is configured to sense cardiac activity and to pace a patient's heart and is disposable within a ventricle of the patient's heart. The LCP includes a housing, a first electrode that is secured relative to the housing and a second electrode that is secured relative to the housing and is spaced from the first electrode. A controller is disposed within the housing and is operably coupled to the first electrode and the second electrode such that the controller is capable of receiving, via the first electrode and the second electrode, electrical cardiac signals of the heart. A pressure sensor may be disposed relative to the housing and may be operably coupled to the controller, the controller configured to receive signals from the pressure sensor. An accelerometer may be disposed relative to the housing and may be operably coupled to the controller, the controller configured to receive signals from the accelerometer. The controller may be configured to determine an atrial contraction timing fiducial based at least in part upon two or more of a signal received from the pressure sensor, a signal received from the accelerometer representing a heart sound and/or endocardial acceleration, and an electrical cardiac signal received via the first electrode and the second electrode and then to generate and deliver a ventricle pacing pulse using the atrial contraction timing fiducial.

Alternatively or additionally to any of the embodiments above, the controller may be configured to determine the atrial contraction timing fiducial based at least in part upon a signal received from the pressure sensor and a signal received from the accelerometer.

Alternatively or additionally to any of the embodiments above, the controller may be configured to determine the atrial contraction timing fiducial based at least in part upon a signal received from the pressure sensor and an electrical cardiac signal received via the first electrode and the second electrode.

Alternatively or additionally to any of the embodiments above, the controller may be configured to determine the atrial contraction timing fiducial based at least in part upon a sensed A-wave in the signal received from the pressure sensor and a sensed signal associated with an S4 heart sound in the signal received from the accelerometer.

Alternatively or additionally to any of the embodiments above, the signal received from the pressure sensor may include a change in ventricle pressure relative to time (dP/dt).

Alternatively or additionally to any of the embodiments above, the signal received from the pressure sensor may include an A-wave.

Alternatively or additionally to any of the embodiments above, the signal received from the pressure sensor may include a pulse pressure.

Alternatively or additionally to any of the embodiments above, the signal received from the accelerometer may include a heart sound signal or an endocardial acceleration signal.

Alternatively or additionally to any of the embodiments above, the electrical cardiac signal received via the first electrode and the second electrode may include at least a portion of an electrocardiogram (ECG).

Alternatively or additionally to any of the embodiments above, the electrical cardiac signal received via the first electrode and the second electrode may include a P-wave.

Alternatively or additionally to any of the embodiments above, the electrical cardiac signal received via the first electrode and the second electrode may include a QRS complex, from which a QRS width can be determined.

Alternatively or additionally to any of the embodiments above, the electrical cardiac signal received via the first electrode and the second electrode may include two consecutive R waves, from which an R-wave to R-wave interval can be determined.

In another example of the disclosure, a leadless cardiac pacemaker (LCP) is configured to sense cardiac activity and to pace a patient's heart and is disposable within a ventricle of the patient's heart. The LCP includes a housing, a first electrode that is secured relative to the housing and a second electrode that is secured relative to the housing and is spaced from the first electrode. A controller is disposed within the housing and is operably coupled to the first electrode and the second electrode such that the controller is capable of receiving, via the first electrode and the second electrode, electrical cardiac signals of the heart. The controller may be configured to determine an atrial contraction timing fiducial based at least in part upon a sensed indication of atrial contraction in a first heartbeat and a sensed indication of ventricular contraction in the first heartbeat, an immediately preceding heartbeat and/or an immediately succeeding heartbeat and to generate and deliver a ventricle pacing pulse using the atrial contraction timing fiducial.

Alternatively or additionally to any of the embodiments above, the LCP may further include a pressure sensor disposed relative to the housing and operably coupled to the controller.

Alternatively or additionally to any of the embodiments above, the LCP may further include an accelerometer disposed relative to the housing and operably coupled to the controller.

Alternatively or additionally to any of the embodiments above, the first signal that provides an indication of atrial contraction may include one or more of an S3 heart sound signal, an S4 heart sound signal, an A-wave signal and/or a P-wave signal.

Alternatively or additionally to any of the embodiments above, the second signal that provides an indication of ventricular contraction may include one or more of a pulse pressure signal, a dP/dt signal, an R-wave to R-wave interval, a QRS complex width, and/or a ventricle pressure-volume loop parameter.

In another example of the disclosure, a method of generating a ventricle pacing pulse using a leadless cardiac pacemaker (LCP) disposed within a patient's left ventricle includes sensing for a first signal indicating an atrial contraction of a patient's heart and sensing for a second different signal related to the atrial contraction of the patient's heart. An atrial contraction timing fiducial may be determined based at least in part on the sensed first signal indicating the atrial contraction of the patient's heart and the sensed second signal related to the atrial contraction of the patient's heart. A ventricle pacing pulse may be generated and delivered using the atrial contraction timing fiducial.

Alternatively or additionally to any of the embodiments above, the second signal related to the atrial contraction of the patient's heart may include an indication of a ventricular contraction of the patient's heart following the atrial contraction of the patient's heart.

Alternatively or additionally to any of the embodiments above, at least one of the first signal and the second signal are generated via a pressure sensor of the LCP.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
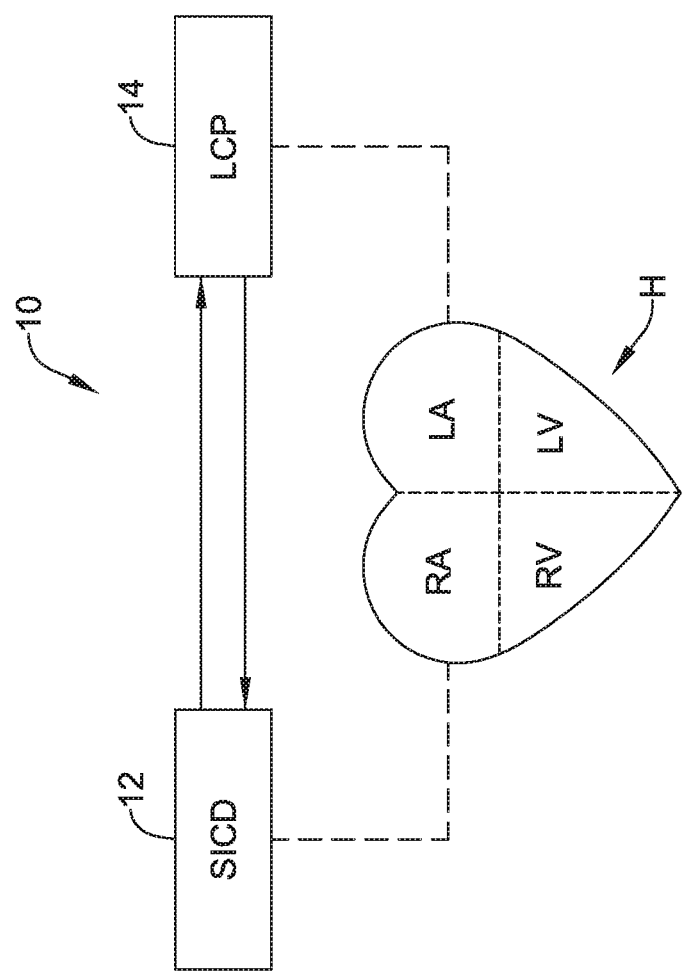
FIG. 1 is a highly schematic diagram of an illustrative system in accordance with an example of the disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

A normal, healthy heart induces contraction by conducting intrinsically generated electrical signals throughout the heart. These intrinsic signals cause the muscle cells or tissue of the heart to contract in a coordinated manner. These contractions forces blood out of and into the heart, providing circulation of the blood throughout the rest of the body. Many patients suffer from cardiac conditions that affect the efficient operation of their hearts. For example, some hearts develop diseased tissue that no longer generate or efficiently conduct intrinsic electrical signals. In some examples, diseased cardiac tissue may conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate, even resulting in cardiac fibrillation. Implantable medical device are often used to treat such conditions by delivering one or more types of electrical stimulation therapy to the patient's heart.

FIG. 1 is a schematic diagram showing an illustrative system 10 that may be used to sense and/or pace a heart H. In some cases, the system 10 may also be configured to be able to shock the heart H. The heart H includes a right atrium RA and a right ventricle RV. The heart H also includes a left atrium LA and a left ventricle LV. In some cases, the illustrative system 10 includes an SICD (subcutaneous implantable cardioverter defibrillator) 12. While not shown in this Figure, in some cases the SICD 12 may include a lead that may be configured to be placed subcutaneously relative to a patient's sternum and outside of the patient's heart. In some cases, the lead may extend around or through the sternum and may be fixed adjacent an inner surface of the sternum and outside of the patient's heart. The SICD 12 may be configured to sense electrical activity generated by the heart H as well as provide electrical energy to the heart H in order to shock the heart H from an undesired heart rhythm to a desired heart rhythm.

In some cases, the system 10 may include an LCP 14 that may be configured to sense and/or pace the heart H. While a single LCP 14 is illustrated, it will be appreciated that two or more LCPs 14 may be implanted in or on the heart H. The LCP 14 may be implanted into any chamber of the heart, such as the right atrium RA, the left atrium LA, the right ventricle RV and the left ventricle LV. When more than one LCP is provided, each LCP may be implanted in a different chamber. In some cases, multiple LCP's may be implanted within a single chamber of the heart H.

In some cases, the SICD 12 and the LCP 14 may be implanted at the same time. In some instances, depending on the cardiac deficiencies of a particular patient, the SICD 12 may be implanted first, and one or more LCPs 14 may be implanted at a later date if/when the patient's heart decompensates and it becomes necessary to pace the heart H. In some cases, it is contemplated that one or more LCPs 14 may be implanted first, in order to sense and pace the heart H. When a need for possible defibrillation becomes evident, the SICD 12 may subsequently be implanted. Regardless of implantation order or sequence, it will be appreciated that the SICD 12 and the LCP 14 may communicate with each other using any desired communications protocol, such as conducted communication through the patient's body.

Figure 2:
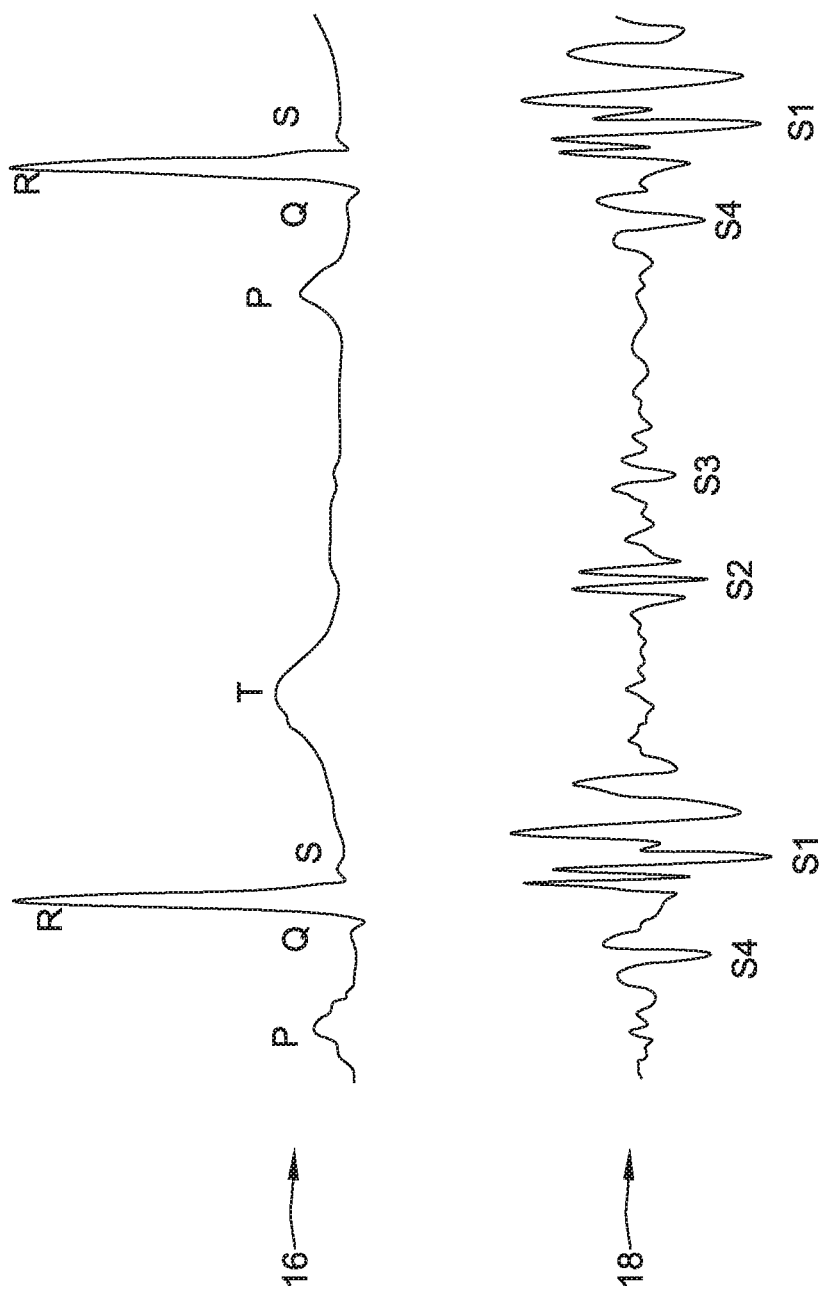
FIG. 2 is a graphical representation of an electrocardiogram (ECG) showing a temporal relationship between electrical signals of the heart and mechanical indications of contraction of the heart.

With reference to FIG. 2, it will be appreciated that the heart H is controlled via electrical signals that pass through the cardiac tissue and that can be detected by implanted devices such as but not limited to the SICD 12 and/or the LCP 14 of FIG. 1. FIG. 2 includes a portion of an electrocardiogram (ECG) 16 along with a heart sounds trace 18. As can be seen in the ECG 16, a heartbeat includes a P-wave that indicates atrial depolarization. A QRS complex, including a Q-wave, an R-wave and an S-wave, represents ventricular depolarization. A T-wave indicates repolarization of the ventricles. It will be appreciated that the ECG 16 may be detected by implanted devices such as but not limited to the SICD 12 and/or the LCP 14 of FIG. 1.

A number of heart sounds may also be detectable while the heart H beats. It will be appreciated that the heart sounds may be considered as on example of mechanical indications of the heart beating. Other illustrative mechanical indications may include, for example, endocardial acceleration or movement of a heart wall detected by an accelerometer in the LCP, acceleration or movement of a heart wall detected by an accelerometer in the SICD, a pressure, pressure change, or pressure change rate in a chamber of the heart H detected by a pressure sensor of the LCP, acoustic signals caused by heart movements detected by an acoustic sensor (e.g. accelerometer, microphone, etc.) and/or any other suitable indication of a heart chamber beating.

An electrical signal typically instructs a portion of the heart H to contract, and then there is a corresponding mechanical indication. In some cases, there may be a first heart sound that is denoted S1 and that is produced by vibrations generated by closure of the mitral and tricuspid valves during a ventricle contraction, a second heart sound that is denoted S2 and that is produced by closure of the aortic and pulmonary valves, a third heart sound that is denoted S3 and that is an early diastolic sound caused by the rapid entry of blood from the right atrium RA into the right ventricle RV and from the left atrium LA into the left ventricle LV, and a fourth heart sound that is denoted S4 and that is a late diastolic sound corresponding to late ventricular filling during an active atrial contraction.

Because the heart sounds are a result of cardiac muscle contracting or relaxing in response to an electrical signal, it will be appreciated that there is a delay between the electrical signal, indicated by the ECG 16, and the corresponding mechanical indication, indicated in the example shown by the heart sounds trace 18. For example, the P-wave of the ECG 16 is an electrical signal triggering an atrial contraction. The S4 heart sound is the mechanical signal caused by the atrial contraction. In some cases, it may be possible to use this relationship between the P-wave and the S4 heart sound. For example, if one of these signals may be detected, the relationship can be used as a timing mechanism to help search for the other. For example, if the P-wave can be detected, a window following the P-wave can be defined and searched in order to find and/or isolate the corresponding S4 heart sound. In some cases, detection of both signals may be an indication of an increased confidence level in a detected atrial contraction. In some cases, detection of either signal may be sufficient to identify an atrial contraction. The identity of an atrial contraction may be used to identify an atrial contraction timing fiducial (e.g. a timing marker of the atrial contraction).

Figure 3:
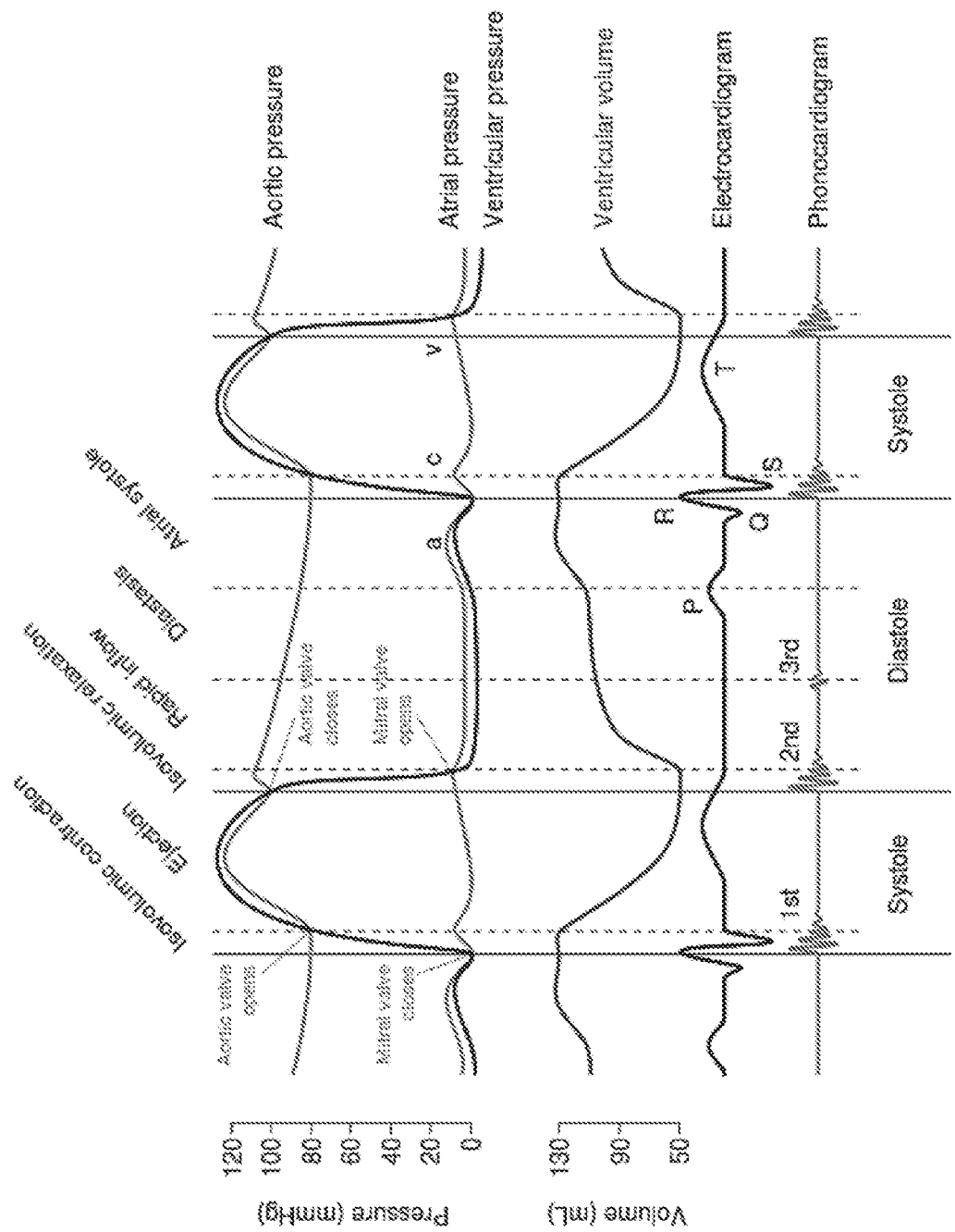
FIG. 3 is a graph showing example pressures and volumes within the heart over time.

In some cases, the relationship of certain electrical signals and/or mechanical indications may be used to predict the timing of other electrical signals and/or mechanical indications within the same heartbeat. Alternatively, or in addition, the timing of certain electrical signals and/or mechanical indications corresponding to a particular heartbeat may be used to predict the timing of other electrical signals and/or mechanical indications within a subsequent heartbeat. It will be appreciated that as the heart H undergoes a cardiac cycle, the blood pressures and blood volumes within the heart H will vary over time. FIG. 3 illustrates how these parameters match up with the electrical signals and corresponding mechanical indications.

FIG. 3 is a graph showing example pressures and volumes within a heart over time. More specifically, FIG. 3 shows an illustrative example of the aortic pressure, left ventricular pressure, left atrial pressure, left ventricular volume, an electrocardiogram (ECG or egram), and heart sounds of the heart H over two consecutive heart beats. A cardiac cycle may begin with diastole, and the mitral valve opens. The ventricular pressure falls below the atrial pressure, resulting in the ventricular filling with blood. During ventricular filling, the aortic pressure slowly decreases as shown. During systole, the ventricle contracts. When ventricular pressure exceeds the atrial pressure, the mitral valve closes, generating the S1 heart sound. Before the aortic valve opens, an isovolumetric contraction phase occurs where the ventricle pressure rapidly increases but the ventricle volume does not significantly change. Once the ventricular pressure equals the aortic pressure, the aortic valve opens and the ejection phase begins where blood is ejected from the left ventricle into the aorta. The ejection phase continues until the ventricular pressure falls below the aortic pressure, at which point the aortic valve closes, generating the S2 heart sound. At this point, the isovolumetric relaxation phase begins and ventricular pressure falls rapidly until it is exceeded by the atrial pressure, at which point the mitral valve opens and the cycle repeats. Cardiac pressure curves for the pulmonary artery, the right atrium, and the right ventricle, and the cardiac volume curve for the right ventricle, may be similar to those illustrated in FIG. 3. In many cases, the cardiac pressure in the right ventricle is lower than the cardiac pressure in the left ventricle.

Figure 4:
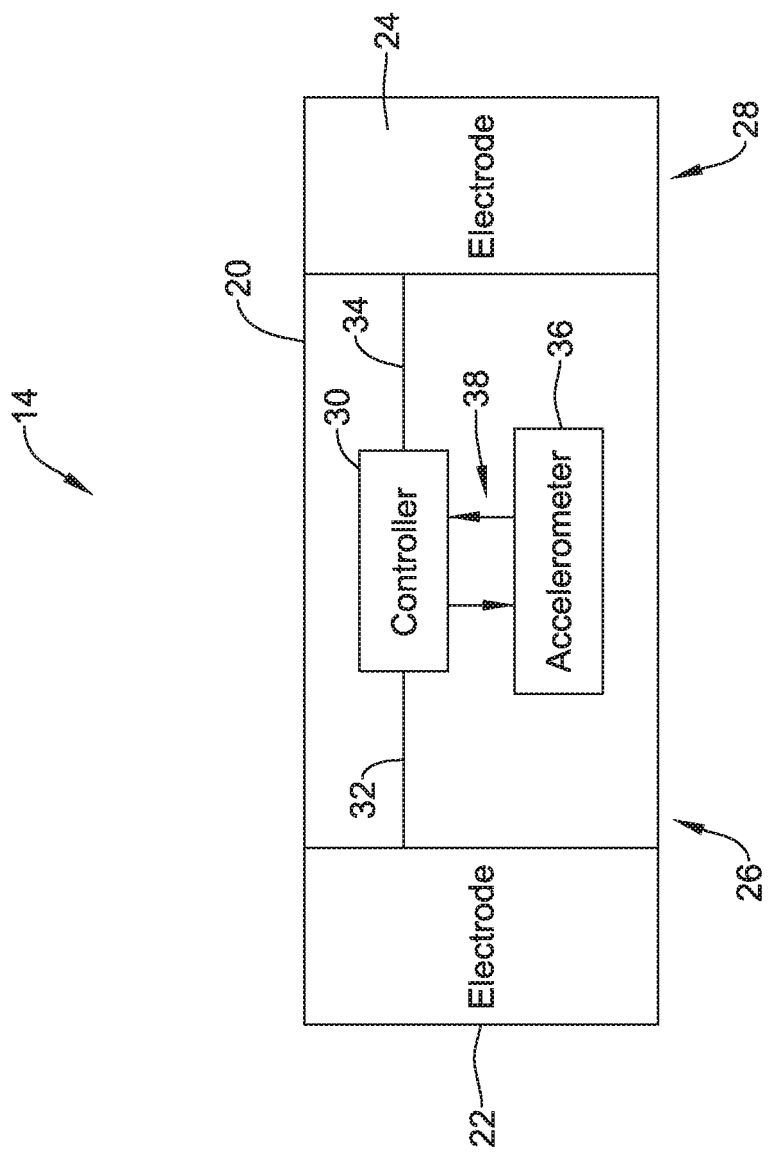
FIG. 4 is a schematic block diagram of an illustrative leadless cardiac pacemaker (LCP) useable in the system of FIG. 1.

FIG. 4 is a schematic diagram of an illustrative LCP 14. In some cases, as indicated, the LCP 14 may be considered as being configured to sense cardiac activity and to pace a patient's heart H. In some cases, the LCP 14 may be disposable within a ventricle of the heart H, such as the right ventricle RV or the left ventricle LV. The LCP 14 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 14 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals that include an electrical indication of an atrial (or other) contraction (e.g. a P-wave of an ECG 16, see FIG. 2). In some cases, the controller 30 may receive electrical signals (e.g. conducted communication signals) that include an indication of atrial (or other) contractions from a remote device such as the SICD 12 (FIG. 1). In some cases, the controller 30 may also be configured to determine an atrial contraction timing fiducial based at least in part upon a sensed indication of atrial contraction in a first heartbeat and/or a sensed indication of ventricular contraction in the first heartbeat, an immediately preceding heartbeat and/or an immediately succeeding heartbeat. In some cases, the controller 30 may be configured to generate and deliver a ventricle pacing pulse using the atrial contraction timing fiducial (e.g. after an A-V delay).

In some cases, the LCP 14 may include an accelerometer 36 that is disposed within the housing 20 and that is operably coupled to the controller 30 via electrical connections 38. In some cases, as discussed further with respect to subsequent Figures, the LCP 14 may include an optional pressure sensor. In some cases, the controller 30 may be configured to detect, via a signal from the accelerometer 36, a mechanical indication of atrial (or other) contraction. In some cases, the mechanical indication of atrial contraction may include but is not limited to an S4 heart sound. While the LCP 14 is shown as including an accelerometer, it will be appreciated that other sensors may be able to provide a signal representing a mechanical indication of atrial (or other) contraction. For example, in some cases the LCP 14 may include a microphone. In some cases, the LCP 14 may include a sonomicrometer, a cardiomechanical sensor that includes, for example, embedded piezoelectric material, or other piezoelectric sensors. In some cases, the LCP may include a pressure sensor for sensing an indication of atrial contraction. These are just examples.

In some cases, signals that provide an indication of atrial contraction may include one or more of an S3 heart sound signal, an S4 heart sound signal, an A-wave signal and/or a P-wave signal. In some cases, signals that provide an indication of ventricular contraction may include one or more of a pulse pressure signal, a dP/dt signal, an R-wave to R-wave interval, a QRS complex width, and/or a ventricle pressure-volume loop parameter. These are just some examples.

Figure 5:
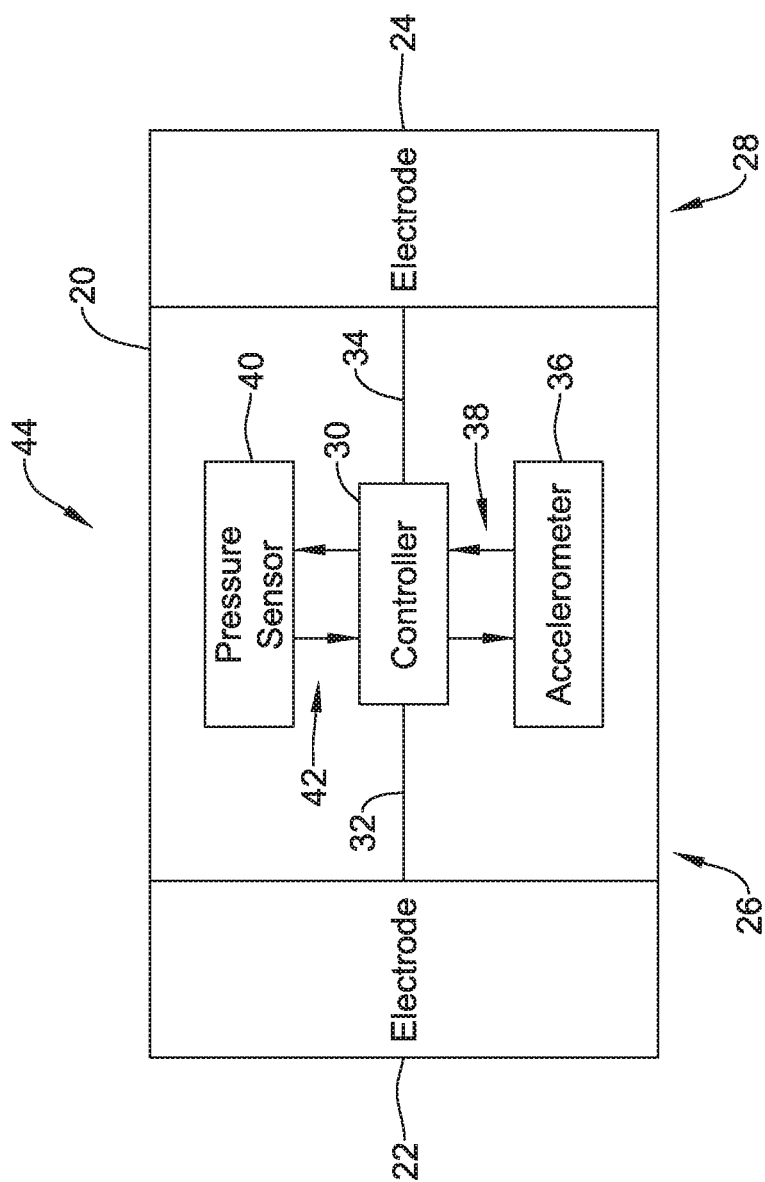
FIG. 5 is a schematic block diagram of an illustrative leadless cardiac pacemaker (LCP) useable in the system of FIG. 1.

FIG. 5 is a schematic diagram of an illustrative LCP 44. In some cases, as indicated, the LCP 44 may be considered as being configured to sense cardiac activity and to pace a patient's heart H. In some cases, the LCP 44 may be disposable within a ventricle of the heart H, such as the right ventricle RV or the left ventricle LV. The LCP 44 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 14 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals that include an electrical indication of an atrial (or other) contraction (e.g. a P-wave of an ECG 16, see FIG. 2). In some cases, detecting a far-field P-wave via the electrodes 22 and 24 of an LCP implanted in the ventricle may have a relatively low signal-to-noise ratio. Detecting the P-wave using the SICD lead may have a higher signal to noise ratio. In some cases, the controller 30 may receive electrical signals (e.g. conducted communication signals)

that include an indication of atrial (or other) contractions from a remote device such as the SICD 12 (FIG. 1).

In some cases, the LCP 44 may include an accelerometer 36 that is disposed within the housing 20 and that is operably coupled to the controller 30 via electrical connections 38. In some cases, the LCP 44 may also include a pressure sensor 40 that is disposed within the housing 20 and that is operably coupled to the controller 30 via electrical connections 42. In some instances, a pressure sensor signal may be responsive to an atrial contraction of the patient's heart. Likewise an accelerometer signal may be responsive to an atrial contraction of the patient's heart.

In some cases, the pressure signal may be used to determine a number of parameters. For example, the pressure signal may be used to determine or detect an A-wave (atrial kick). In another example, the pressure signal may be used to determine or detect a pressure pulse or pressure vibrations associated with S4, which may, for example, be in the 25-30 Hz range. In some cases, the S4 heart sound may be easier to detect using the pressure signal than the accelerometer signal, particularly since the ventricle pressure is not changing substantially at this time (ventricle is filling). In another example, the pressure signal may be used to determine a change in ventricle pressure relative to time (dP/dt).

In some cases, the controller 30 may be configured to detect, via a signal from the accelerometer 36, one or more signals indicating an atrial (or other) contraction. In some cases, the signal received from the accelerometer 36 may include a heart sound signal (e.g. S4) or an endocardial acceleration signal. While the LCP 14 is shown as including an accelerometer 36 and a pressure sensor 40, it will be appreciated that other sensors may also be able to provide a signal representing a mechanical indication of atrial (or other) contraction. For example, in some cases the LCP 14 may include a microphone. In some cases, the LCP 44 may include a sonomicrometer, a cardiomechanical sensor that includes, for example, embedded piezoelectric material, or other piezeoelectric sensors. These are just examples.

In some cases, the controller 30 may also be configured determine an atrial contraction timing fiducial based at least in part upon two or more of a signal received from the pressure sensor 40, a signal received from the accelerometer 36 (e.g. representing a heart sound and/or endocardial acceleration), and an electrical cardiac signal received via the first electrode 22 and the second electrode 24. In some cases, the electrical cardiac signal received via the first electrode 22 and the second electrode 24 may include at least a portion of an electrocardiogram (ECG). In some cases, the electrical cardiac signal received via the first electrode 22 and the second electrode 24 may include a P-wave. In some instances, the electrical cardiac signal received via the first electrode 22 and the second electrode 24 may include a QRS complex, from which a QRS width can be determined. In some cases, the electrical cardiac signal received via the first electrode 22 and the second electrode 24 may include two consecutive R waves, from which an R-wave to R-wave interval can be determined. In some cases, the electrical cardiac signal may include a conducted or other communicated electrical signal from another device (e.g. SICD device) that includes an indication of an atrial or other contraction of the heart H. In some cases, the controller 30 may be configured to generate and deliver a ventricle pacing pulse using the atrial contraction timing fiducial.

In some cases, the controller 30 may be configured to determine the atrial contraction timing fiducial based at least in part upon a signal received from the pressure sensor 40 and a signal received from the accelerometer 36. In some instances, the controller 30 may be configured to determine the atrial contraction timing fiducial based at least in part upon a signal received from the pressure sensor 40 and an electrical cardiac signal received via the first electrode 22 and the second electrode 24. In some cases, the controller 30 may be configured to determine the atrial contraction timing fiducial based at least in part upon a sensed A-wave in the signal received from the pressure sensor 40 and a sensed signal associated with an S4 heart sound in the signal received from the accelerometer 36.

In some instances, the controller 30 may be configured to determine a pace time for delivering a ventricle pacing pulse to the ventricle of the patient's heart H, and the controller 30 may determine the pace time based at least in part on a pressure signal received from the pressure sensor 40. For example, in some cases, the controller may be configured to determine the pace time based at least in part on the received pressure signal and the received accelerometer signal. As another example, in some cases, the controller 30 may be configured to determine the pace time based at least in part on a heart sound or endocardial acceleration represented in the received pressure signal and/or in the received accelerometer signal.

In some cases, the controller 30 may be configured to determine the pace time based at least in part on the received pressure signal and the received electrical cardiac signal. In some instances, the controller 30 may be configured to determine the pace time based at least in part on the received pressure signal, the received accelerometer signal and the received electrical cardiac signal. In some cases, the controller 30 may be configured to determine the pace time based at least in part on a diastolic pressure represented in the received pressure signal. In some cases, the controller 30 may be configured to determine the pace time based at least in part on an A-wave represented in the received pressure signal. In some instances, the controller 30 may be configured to determine the pace time based at least in part on a systolic pressure represented in the received pressure signal. In some cases, the controller 30 may be configured to determine the pace time based at least in part on a dP/dt parameter (e.g. pace at a time to maximize dP/dt in the ventricle) during systole represented in the received pressure signal. In some cases, the controller 30 may be configured to determine the pace time based at least in part on when the received pressure signal crossing a predetermined threshold during systole. In some instances, the controller 30 may be configured to determine the pace time based at least in part on an A-V delay relative to a previously determined atrial contraction timing fiducial, and the controller 30 may adjust the A-V delay based at least in part on one or more of the received pressure signal, the received accelerometer signal and the received electrical cardiac signal during the current, previous and/or subsequent cardiac cycles.

In some instances, the controller 30 may be configured to determine a ventricle pace time for delivering a ventricle pacing pulse to the ventricle of the patient's heart H. For example, in some cases, the controller 30 may determine the ventricle pace time based at least in part on an indication of an atrial contraction event of the patient's heart H and an indication of a current posture of the patient. It will be appreciated that cardiac demand, or the blood pumping needs of the patient, may vary depending on whether the patient is laying down, sitting, standing, etc. In some cases, for example, an indication of an atrial contraction event may be based primarily or exclusively on the received accelerometer signal if the indication of the posture of the patient is reclined, and may be based primarily or exclusively on the received pressure signal if the indication of the posture of the patient is upright. The signal-to-noise ratio may be greater for the accelerometer signal when the patient is at rest (e.g. reclined) and the signal-to-noise ratio may be greater for the pressure signal when the patient is active (e.g. upright). In some cases, the controller 30 may be configured to determine the indication of the posture of the patient based at least in part on the accelerometer signal.

In some instances, the controller 30 may be configured to determine the ventricle pace time based at least in part on an LV pressure parameter indicated in the pressure sensor signal when the indication of the posture of the patient is upright. The controller 30 may, conversely, be configured to determine the ventricle pace time based at least in part on a heart sound indicated in the pressure sensor signal and/or in the accelerometer signal when the indication of the posture of the patient is reclined. In some cases, the controller 30 may be configured to determine the ventricle pace time to achieve lower passive ventricular filling when the indication of the posture of the patient is upright and to determine the ventricle pace time to achieve higher passive ventricular filling when the indication of the posture of the patient is reclined (e.g. maximize diastolic interval, increase S2 to A-wave rise interval, lower heart rate, etc.). This may operate the heart in a manner that reduces stretch stress on the heart while still meeting the current metabolic demands of the patient during times when the metabolic demand is relative low (e.g. reclined), and to operate the heart in a manner that maximizes pumping capacity when the metabolic demand is higher (e.g. upright). This may help reduce the rate at which a patient's heart decompensates by allowing the heart to "rest" more during times of low metabolic demand. While posture may be used as an indicator for metabolic demand, it is contemplated that metabolic demand may be estimated based on any number of other parameters including, for example, heart rate, respiration of the patient, activity level of the patient, posture, blood gas, blood analytes (e.g. lactate or norepinephrine), cardiac conduction velocities (e.g. PR interval or QT interval) and/or sleep state.

Figure 6:
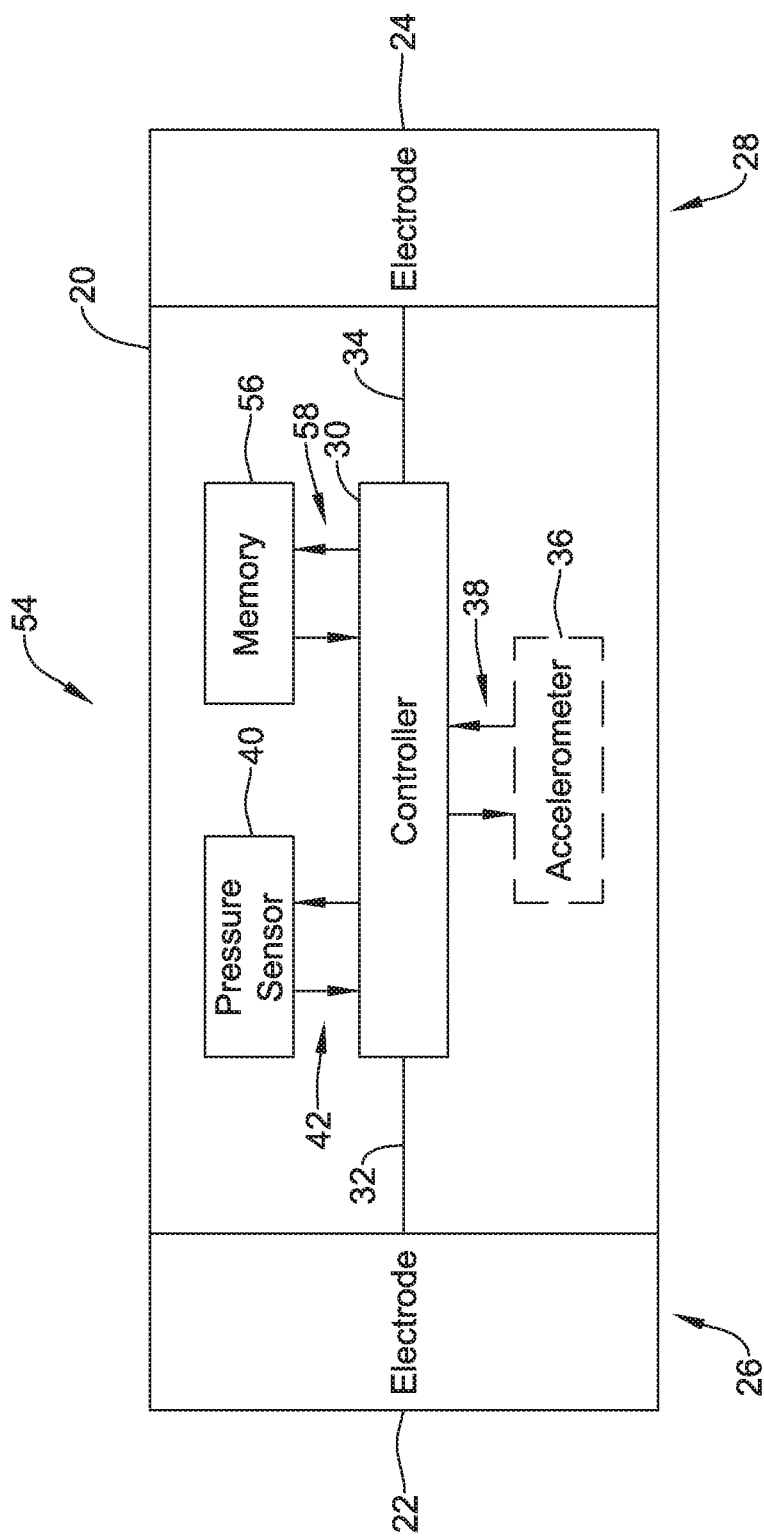
FIG. 6 is a schematic block diagram of an illustrative leadless cardiac pacemaker (LCP) useable in the system of FIG. 1.

FIG. 6 is a schematic diagram of an illustrative LCP 54. In some cases, as indicated, the LCP 54 may be considered as being configured to sense cardiac activity and to pace a patient's heart H. In some cases, the LCP 54 may be disposable within a ventricle of the heart H, such as the right ventricle RV or the left ventricle LV. The LCP 54 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 54 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals representative of cardiac activity. In some cases, the controller 30 may receive signals that include an electrical indication of an atrial (or other) contraction (e.g. a P-wave of an ECG 16, see FIG. 2). In some cases, the controller 30 may receive electrical signals (e.g. conducted communication signals) that include an indication of atrial (or other) contractions from a remote device such as the SICD 12 (FIG. 1).

In some cases, the LCP 54 may include a memory 56 that is operably coupled to the controller 30 via electrical connections 58. In some cases, for example, the memory 56 may be configured to store information pertaining to a previously determined atrial contraction timing fiducial, as well as other information.

In some cases, the LCP 54 may include an accelerometer 36 that is disposed within the housing 20 and that is operably coupled to the controller 30 via electrical connections 38. In some cases, the LCP 54 may further include a pressure sensor 40 that is disposed within the housing 20 and that is operably coupled to the controller 30 via electrical connections 42. The controller 30 may, for example, be configured to receive an accelerometer signal from the accelerometer 36 and/or a pressure sensor signal from the pressure sensor 40. In some instances, for example, the controller 30 may be configured to determine an A-V delay relative to a previously determined atrial contraction timing fiducial based at least in part on a pressure signal from the pressure sensor 40. In some cases, the controller 30 may be configured to adjust the A-V delay based at least in part on the accelerometer signal. In some cases, the controller 30 may be configured to generate a ventricle pacing pulse after the adjusted A-V delay following the previously determined atrial contraction timing fiducial.

In some instances, the pressure signal received by the controller 30 may include a pulse pressure, and the controller 30 may be configured to adjust the A-V delay relative to the previously determined atrial contraction timing fiducial based at least in part on the pulse pressure. In some cases, the pressure signal received by the controller 30 includes a rate of change in pressure over time (dP/dt) and the controller 30 may be configured to adjust the A-V delay relative to the previously determined atrial contraction timing fiducial based at least in part on the dP/dt. In some cases, the A-V delay may be adjusted to maximize the dP/dt sensed in the ventricle. In some cases, the A-V delay may be adjusted to minimize the negative dP/dt sensed in the ventricle in diastole. In some cases, the A-V delay may be adjusted to achieve a minimum ventricle pressure pulse width (e.g. width between maximum dP/dt and maximum negative dP/dt). In some cases, heart sounds in conjunction with the LV pressure waveform may be used to separate out various timing components of the heart H such as ejection time, isovolumetric contraction time, isovolumetric relation time, etc.)

In some instances, the pressure signal received by the controller 30 may include an A-wave signal, and the controller 30 may be configured to progressively reduce the A-V delay until the A-wave signal is not detected, and then progressively increase the A-V delay until the A-wave signal is again just detected and an onset of LV pressure rise is right on top of the A-wave, at which point the A-V delay may be considered to be optimal. In some cases, the controller 30 may be configured to adjust the A-V delay in response to an LV volume related impedance signal received or measured via the first electrode 22 and the second electrode 24, and the controller 30 may adjust the A-V delay relative to the previously determined atrial contraction timing fiducial in order to increase an LV ejection fraction that is estimated using the LV volume related impedance signal.

In some cases, the controller 30 may be configured to adjust the A-V delay in response to an electrical cardiac signal received via the first electrode 22 and the second electrode 24 including a QRS complex, from which a QRS width can be determined, and the controller 30 may be configured to adjust the A-V delay relative to the previously determined atrial contraction timing fiducial in order to minimize the QRS width. In some instances, the controller 30 may be configured to adjust the A-V delay in response to a received signal indicative of mitral regurgitation from the pressure sensor 40 and/or the accelerometer 36, and the controller 30 may be configured to adjust the A-V delay relative to the previously determined atrial contraction timing fiducial in order to minimize detected mitral regurgitation.

Figure 7:
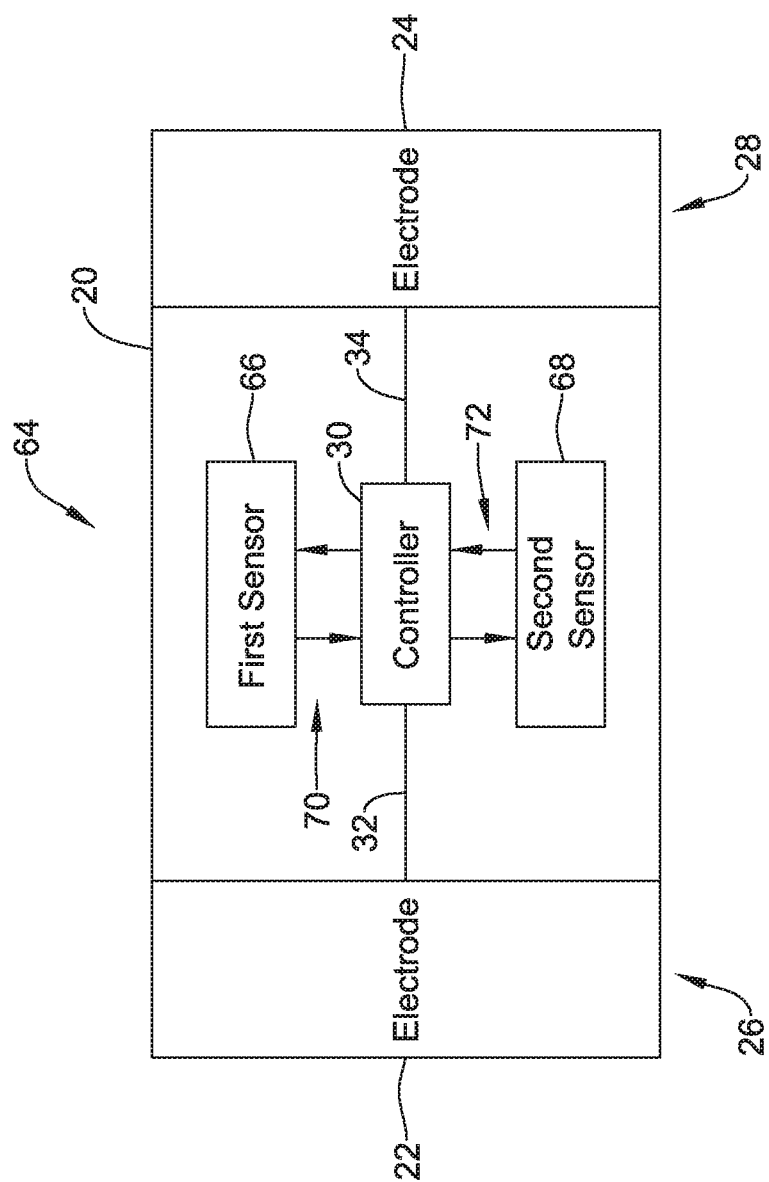
FIG. 7 is a schematic block diagram of an illustrative leadless cardiac pacemaker (LCP) useable in the system of FIG. 1.

FIG. 7 is a schematic diagram of an illustrative LCP 64. In some cases, as indicated, the LCP 64 may be considered as being configured to sense cardiac activity and to pace a patient's heart H. In some cases, the LCP 64 may be disposable within a ventricle of the heart H, such as the right ventricle RV or the left ventricle LV. The LCP 64 may be considered as including a housing 20, a first electrode 22 that is secured relative to the housing 20 and exposed to an environment outside the housing 20 (e.g. blood, tissue, etc.), and a second electrode 24 that is secured relative to the housing 20 and exposed to the environment outside of the housing 20 (e.g. blood, tissue, etc.). The second electrode 24 may be spaced from the first electrode 22. In some cases, as illustrated, the first electrode 22 may be disposed at or near a first end 26 of the housing 20 and the second electrode 24 may be disposed at or near a second end 28 of the housing 20, although this is not required in all cases.

The LCP 64 may further include a controller 30 that is disposed within the housing 20 and that is operably coupled to the first electrode 22 via a first electrical connection 32 and the second electrode 24 via a second electrical connection 34. In some cases, the controller 30 may be capable of receiving, via the first electrode 22 and the second electrode 24, electrical signals representative of cardiac activity. In some cases, the controller 30 may receive signals that include an electrical indication of an atrial (or other) contraction (e.g. a P-wave of an ECG 16, see FIG. 2). In some cases, the controller 30 may receive electrical signals (e.g. conducted communication signals) that include an indication of atrial (or other) contractions from a remote device such as the SICD 12 (FIG. 1).

In some cases, the LCP 64 may include a first sensor 66 and a second sensor 68. The first sensor 66 may be disposed within the housing 20 and may be operably coupled to the controller 30 via electrical connections 70. The second sensor 68 may be disposed within the housing 20 and may be operably coupled to the controller 30 via electrical connections 72. In some cases, the first sensor 66 may include an accelerometer. In some instances, the second sensor 68 may include a pressure sensor. In some cases, the first sensor 66 may provide a first sensor signal to the controller 30, where the first sensor signal is responsive to an atrial contraction of the patient' heart. In some cases, the second sensor 68 may provide a second sensor signal to the controller 30, where the second sensor signal is responsive to an atrial contraction of the patient's heart.

In some cases, a signal from the first sensor 66 may be weighted with a first weight and a signal from the second sensor 68 may be weighted with a second weight. In some cases, for example, the first weight applied to the first signal and/or the second weight applied to the second signal may be based at least in part on a confidence level in the corresponding signals. In some cases, the weights may be based at least in part on the Signal-To-Noise ratio (SNR) of the corresponding signals. In some cases, the controller 30 may, for example, preferentially rely more on the first signal from the first sensor 66 and less on the second signal from the second sensor 68. In some instances, the controller 30 may preferentially rely more on the second signal from the second sensor 68 and less on the first signal from the first sensor 66.

In some cases, the controller 30 may be configured to determine a ventricle pace time for delivering a ventricle pacing pulse to the ventricle of the patient's heart. In some cases, the controller 30 may determine the ventricle pace time based at least in part on an indication of an atrial contraction event of the patient's heart, and in some cases an indication of metabolic demand on the patient's heart. The indication of an atrial contraction event may be based primarily or exclusively on the received first signal if the indication of metabolic demand is below a metabolic demand threshold and may be based primarily or exclusively on the received second signal if the indication of metabolic demand is above the metabolic demand threshold. In some cases, the indication of metabolic demand may be based at least in part upon the received first sensor signal. In some cases, the indication of metabolic demand may be based at least in part upon the received second sensor signal. In some instances, the indication of metabolic demand may be based at least in part upon the received electrical cardiac signal. The controller 30 may be configured to generate a ventricle pacing pulse at the ventricle pace time.

In an example, either the first sensor 66 or the second sensor 68 may be an accelerometer, and the controller 30 may be configured to determine a posture of the patient based at least in part on an accelerometer signal from the accelerometer, and may determine an indication of metabolic demand based at least in part on the determined posture. In another example, either the first sensor 66 or the second sensor 68 may be an accelerometer, and the controller 30 may be configured to determine an activity level of the patient based at least in part on an accelerometer signal from the accelerometer, and to determine the indication of metabolic demand based at least in part on the determined activity level.

In another example, the first sensor 66 and the second sensor 68 may include an accelerometer and a pressure sensor, and the controller 30 may be configured to attempt to detect an A-wave via a pressure signal from the pressure sensor. The controller 30 may also determine a ventricle pace time based at least in part on: (1) the A-wave when the A-wave is detected; and (2) one or more of a received pressure signal from the pressure sensor and/or a received accelerometer signal from the accelerometer other than the A-wave when the A-wave is not detected. In another example of the first sensor 66 and the second sensor 68 including an accelerometer and a pressure sensor, the controller 30 may be configured to determine a ventricle pace time based at least in part on an LV pressure parameter indicated in a pressure signal of the pressure sensor when the indication of metabolic demand is above the metabolic demand threshold and to determine the ventricle pace time based at least in part on a heart sound indicated in the pressure signal of the pressure sensor and/or in an accelerometer signal of the accelerometer when the indication of metabolic demand is below the metabolic demand threshold.

In another example of the first sensor 66 and the second sensor 68 including an accelerometer and a pressure sensor, the controller 30 may be configured to detect an S2 heart sound via the pressure sensor and/or the accelerometer and detect an A-wave via the pressure sensor. In some cases, the controller 30 may be configured to determine a ventricle pace time to achieve a smaller S2 to A-wave interval when the indication of metabolic demand exceeds a relaxation threshold and to achieve a larger S2 to A-wave interval when the indication of metabolic demand does not exceed the relaxation threshold. In some cases, the controller 30 may be configured to detect an S2 heart sound via the pressure sensor and/or the accelerometer and to detect an S1 heart sound via the pressure sensor and/or the accelerometer. In some instances, the controller 30 may be configured to determine a ventricle pace time to achieve a smaller S2 to S1 interval when the indication of metabolic demand exceeds a relaxation threshold and to determine the ventricle pace time to achieve a larger S2 to S1 interval when the indication of metabolic demand does not exceed the relaxation threshold. The relaxation threshold is set to correspond to when the patient is in a relaxation (versus active) state.

In some cases, either the first sensor 66 or the second sensor 68 may include a pressure sensor, and the controller 30 may be configured to determine a ventricle pace time to achieve a higher change rate in LV pressure over time (dP/dt) when the indication of metabolic demand is above a relaxation threshold, and to determine a ventricle pace time to achieve a lower change rate in LV pressure over time (dP/dt) when the indication of metabolic demand is below the relaxation threshold. In yet another example, the controller 30 may be configured to determine a ventricle pace time to achieve lower passive ventricular filling when the indication of metabolic demand is above a relaxation threshold, and to determine a ventricle pace time to achieve higher passive ventricular filling when the indication of metabolic demand is below a relaxation threshold.

It is contemplated that the above-referenced relaxation threshold may not be a single threshold. For example, in some cases, the relaxation threshold may include hysteresis, where a different relaxation threshold is applied depending on whether the patient is transitioning from a relaxed state to an active state, or from an active state to a relaxed state.

Figure 8:
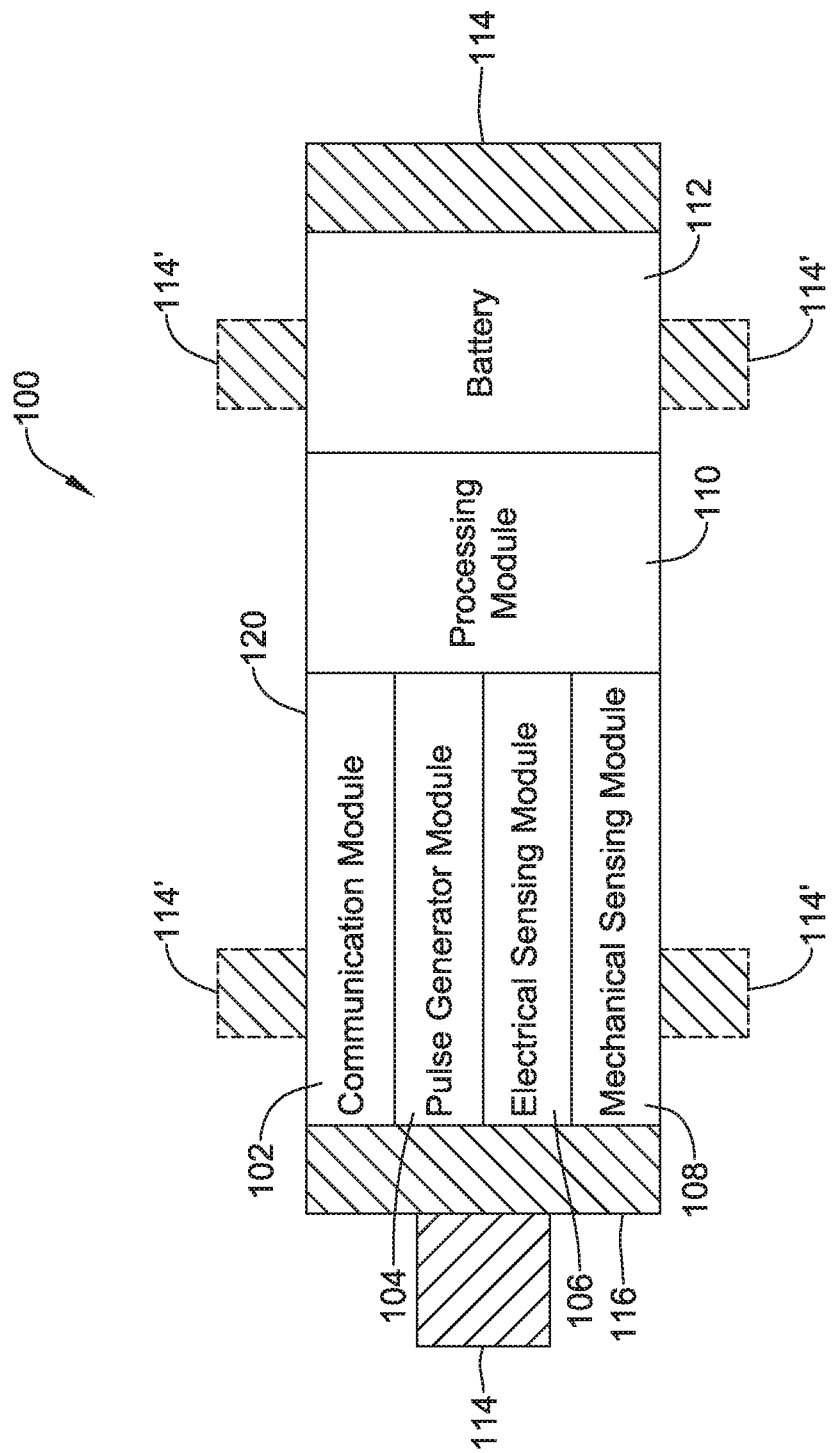
FIG. 8 is a schematic block diagram of an illustrative LCP in accordance with an example of the disclosure.

FIG. 8 depicts another illustrative leadless cardiac pacemaker (LCP) that may be implanted into a patient and may operate to deliver appropriate therapy to the heart, such as to deliver anti-tachycardia pacing (ATP) therapy, cardiac resynchronization therapy (CRT), bradycardia therapy, and/or the like. As can be seen in FIG. 8, the LCP 100 may be a compact device with all components housed within the or directly on a housing 120. In some cases, the LCP 100 may be considered as being an example of one or more of the LCP 14 (FIGS. 1 and 3), the LCP 44 (FIG. 5), the LCP 54 (FIG. 6) and/or the LCP 64 (FIG. 7). In the example shown in FIG. 8, the LCP 100 may include a communication module 102, a pulse generator module 104, an electrical sensing module 106, a mechanical sensing module 108, a processing module 110, a battery 112, and an electrode arrangement 114. The LCP 100 may include more or less modules, depending on the application.

The communication module 102 may be configured to communicate with devices such as sensors, other medical devices such as an SICD, and/or the like, that are located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, instructions and/or messages from the external medical device through the communication module 102, and the LCP 100 may use the received signals, data, instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication.

In the example shown in FIG. 8, the pulse generator module 104 may be electrically connected to the electrodes 114. In some examples, the LCP 100 may additionally include electrodes 114'. In such examples, the pulse generator 104 may also be electrically connected to the electrodes 114'. The pulse generator module 104 may be configured to generate electrical stimulation signals. For example, the pulse generator module 104 may generate and deliver electrical stimulation signals by using energy stored in the battery 112 within the LCP 100 and deliver the generated electrical stimulation signals via the electrodes 114 and/or 114'. Alternatively, or additionally, the pulse generator 104 may include one or more capacitors, and the pulse generator 104 may charge the one or more capacitors by drawing energy from the battery 112. The pulse generator 104 may then use the energy of the one or more capacitors to deliver the generated electrical stimulation signals via the electrodes 114 and/or 114'. In at least some examples, the pulse generator 104 of the LCP 100 may include switching circuitry to selectively connect one or more of the electrodes 114 and/or 114' to the pulse generator 104 in order to select which of the electrodes 114/114' (and/or other electrodes) the pulse generator 104 delivers the electrical stimulation therapy. The pulse generator module 104 may generate and deliver electrical stimulation signals with particular features or in particular sequences in order to provide one or multiple of a number of different stimulation therapies. For example, the pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or to produce any other suitable electrical stimulation therapy. Some more common electrical stimulation therapies include anti-tachycardia pacing (ATP) therapy, cardiac resynchronization therapy (CRT), and cardioversion/defibrillation therapy.

In some examples, the LCP 100 may not include a pulse generator 104. For example, the LCP 100 may be a diagnostic only device. In such examples, the LCP 100 may not deliver electrical stimulation therapy to a patient. Rather, the LCP 100 may collect data about cardiac electrical activity and/or physiological parameters of the patient and communicate such data and/or determinations to one or more other medical devices via the communication module 102.

In some examples, the LCP 100 may include an electrical sensing module 106, and in some cases, a mechanical sensing module 108. The electrical sensing module 106 may be configured to sense the cardiac electrical activity of the heart. For example, the electrical sensing module 106 may be connected to the electrodes 114/114', and the electrical sensing module 106 may be configured to receive cardiac electrical signals conducted through the electrodes 114/114'. The cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' may represent ventricular cardiac electrical signals. In some cases, the LCP 100 may be configured to detect cardiac electrical signals from other chambers (e.g. far field), such as the P-wave from the atrium.

The mechanical sensing module 108 may include one or more sensors, such as an accelerometer, a pressure sensor, a heart sound sensor, a blood-oxygen sensor, a chemical sensor, a temperature sensor, a flow sensor and/or any other suitable sensors that are configured to measure one or more mechanical/chemical parameters of the patient. Both the electrical sensing module 106 and the mechanical sensing module 108 may be connected to a processing module 110, which may provide signals representative of the sensed mechanical parameters. Although described with respect to FIG. 8 as separate sensing modules, in some cases, the electrical sensing module 206 and the mechanical sensing module 208 may be combined into a single sensing module, as desired.

The electrodes 114/114' can be secured relative to the housing 120 but exposed to the tissue and/or blood surrounding the LCP 100. In some cases, the electrodes 114 may be generally disposed on either end of the LCP 100 and may be in electrical communication with one or more of the modules 102, 104, 106, 108, and 110. The electrodes 114/114' may be supported by the housing 120, although in some examples, the electrodes 114/114' may be connected to the housing 120 through short connecting wires such that the electrodes 114/114' are not directly secured relative to the housing 120. In examples where the LCP 100 includes one or more electrodes 114', the electrodes 114' may in some cases be disposed on the sides of the LCP 100, which may increase the number of electrodes by which the LCP 100 may sense cardiac electrical activity, deliver electrical stimulation and/or communicate with an external medical device. The electrodes 114/114' can be made up of one or more biocompatible conductive materials such as various metals or alloys that are known to be safe for implantation within a human body. In some instances, the electrodes 114/114' connected to the LCP 100 may have an insulative portion that electrically isolates the electrodes 114/114' from adjacent electrodes, the housing 120, and/or other parts of the LCP 100. In some cases, one or more of the electrodes 114/114' may be provided on a tail (not shown) that extends away from the housing 120.

The processing module 110 can be configured to control the operation of the LCP 100. For example, the processing module 110 may be configured to receive electrical signals from the electrical sensing module 106 and/or the mechanical sensing module 108. Based on the received signals, the processing module 110 may determine, for example, abnormalities in the operation of the heart H. Based on any determined abnormalities, the processing module 110 may control the pulse generator module 104 to generate and deliver electrical stimulation in accordance with one or more therapies to treat the determined abnormalities. The processing module 110 may further receive information from the communication module 102. In some examples, the processing module 110 may use such received information to help determine whether an abnormality is occurring, determine a type of abnormality, and/or to take particular action in response to the information. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The battery 112 may provide power to the LCP 100 for its operations. In some examples, the battery 112 may be a non-rechargeable lithium-based battery. In other examples, a non-rechargeable battery may be made from other suitable materials, as desired. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the battery 112 may a rechargeable battery, which may help increase the useable lifespan of the LCP 100. In still other examples, the battery 110 may be some other type of power source, as desired.

To implant the LCP 100 inside a patient's body, an operator (e.g., a physician, clinician, etc.), may fix the LCP 100 to the cardiac tissue of the patient's heart. To facilitate fixation, the LCP 100 may include one or more anchors 116. The anchor 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 9:
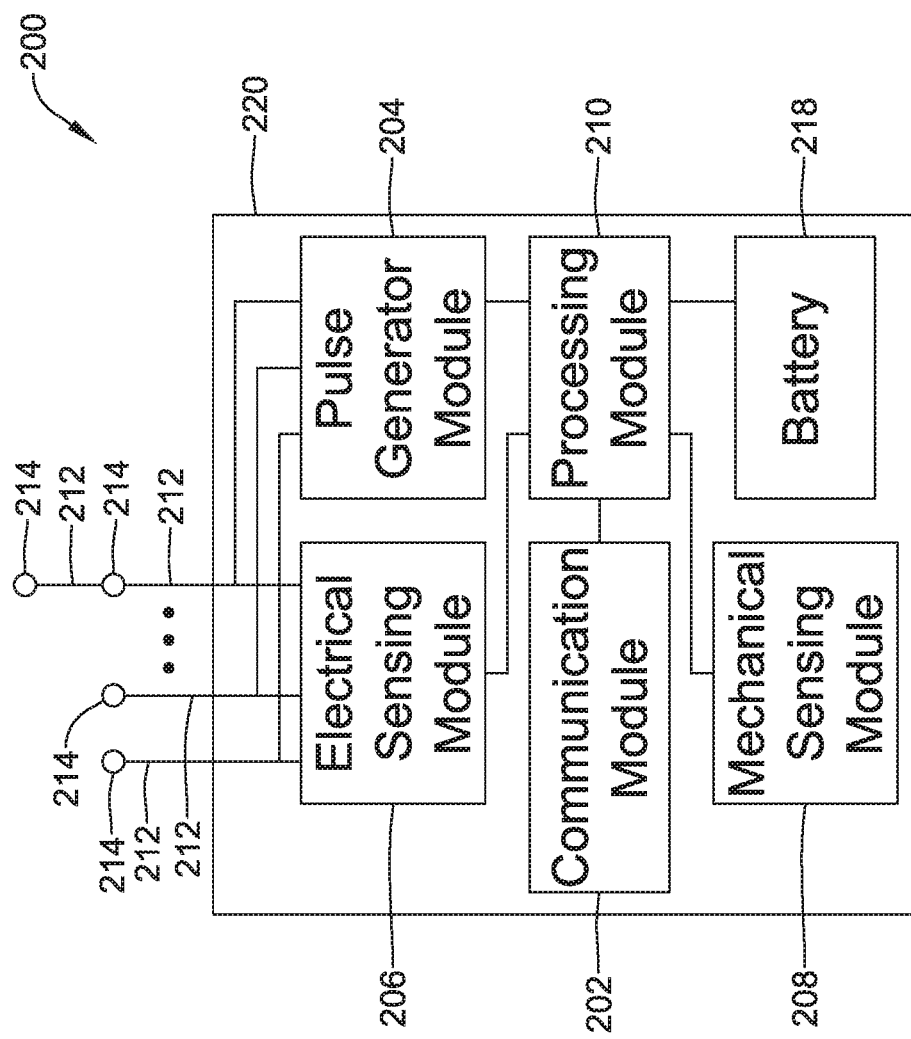
FIG. 9 is a schematic block diagram of another illustrative medical device that may be used in conjunction with the LCP of FIG. 8.

FIG. 9 depicts an example of another medical device (MD) 200, which may be used in conjunction with the LCP 100 (FIG. 8) in order to detect and/or treat cardiac abnormalities. In some cases, the MD 200 may be considered as an example of the SICD 12 (FIG. 1). In the example shown, the MD 200 may include a communication module 202, a pulse generator module 204, an electrical sensing module 206, a mechanical sensing module 208, a processing module 210, and a battery 218. Each of these modules may be similar to the modules 102, 104, 106, 108, and 110 of LCP 100. Additionally, the battery 218 may be similar to the battery 112 of the LCP 100. In some examples, however, the MD 200 may have a larger volume within the housing 220. In such examples, the MD 200 may include a larger battery and/or a larger processing module 210 capable of handling more complex operations than the processing module 110 of the LCP 100.

While it is contemplated that the MD 200 may be another leadless device such as shown in FIG. 8, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and delivery the signals to the patient's heart (either directly or indirectly).

The mechanical sensing module 208, as with the mechanical sensing module 108, may contain or be electrically connected to one or more sensors, such as accelerometers, acoustic sensors, blood pressure sensors, heart sound sensors, blood-oxygen sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (ICP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some instances, the lead(s) may have one or more electrodes that are placed subcutaneously and outside of the chest cavity. In other examples, the lead(s) may have one or more electrodes that are placed inside of the chest cavity, such as just interior of the sternum.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy.

Figure 10:
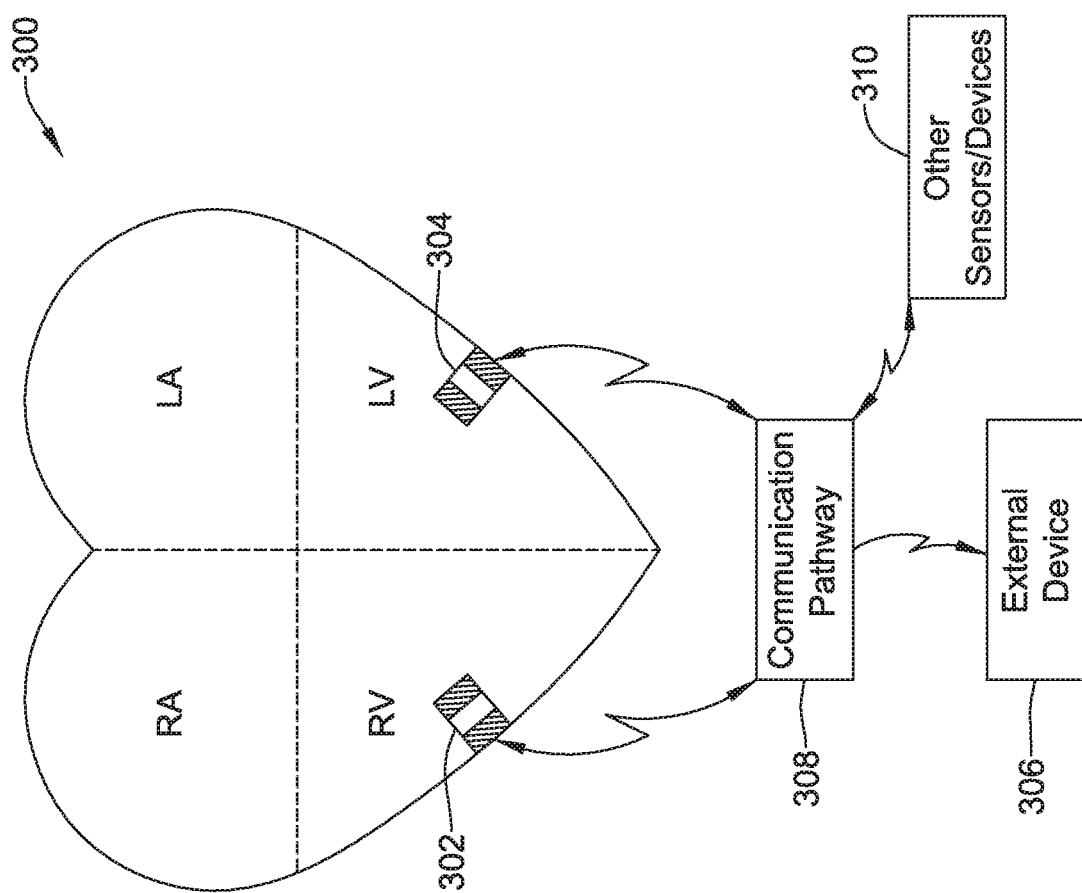
FIG. 10 is a schematic diagram of an exemplary medical system that includes multiple LCPs and/or other devices in communication with one another.

FIG. 10 illustrates an example of a medical device system and a communication pathway through which multiple medical devices 302, 304, 306, and/or 310 may communicate. In the example shown, the medical device system 300 may include LCPs 302 and 304, external medical device 306, and other sensors/devices 310. The external device 306 may be any of the devices described previously with respect to the MD 200. Other sensors/devices 310 may also be any of the devices described previously with respect to the MD 200. In some instances, other sensors/devices 310 may include a sensor, such as an accelerometer, an acoustic sensor, a blood pressure sensor, or the like. In some cases, other sensors/devices 310 may include an external programmer device that may be used to program one or more devices of the system 300.

Various devices of the system 300 may communicate via communication pathway 308. For example, the LCPs 302 and/or 304 may sense intrinsic cardiac electrical signals and may communicate such signals to one or more other devices 302/304, 306, and 310 of the system 300 via communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient. It is contemplated that the communication pathway 308 may communicate using RF signals, inductive coupling, optical signals, acoustic signals, or any other signals suitable for communication. Additionally, in at least some examples, device communication pathway 308 may include multiple signal types. For instance, other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through other sensors/devices 310, where the LCPs 302/304 send signals to other sensors/devices 310, and other sensors/devices 310 relay the received signals to the external device 306.

In some cases, the communication pathway 308 may include conducted communication. Accordingly, devices of the system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-threshold to the heart. Although, in some cases, the amplitude/pulse width of the delivered electrical communication pulses may be above the capture threshold of the heart, but may be delivered during a blanking period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 11:
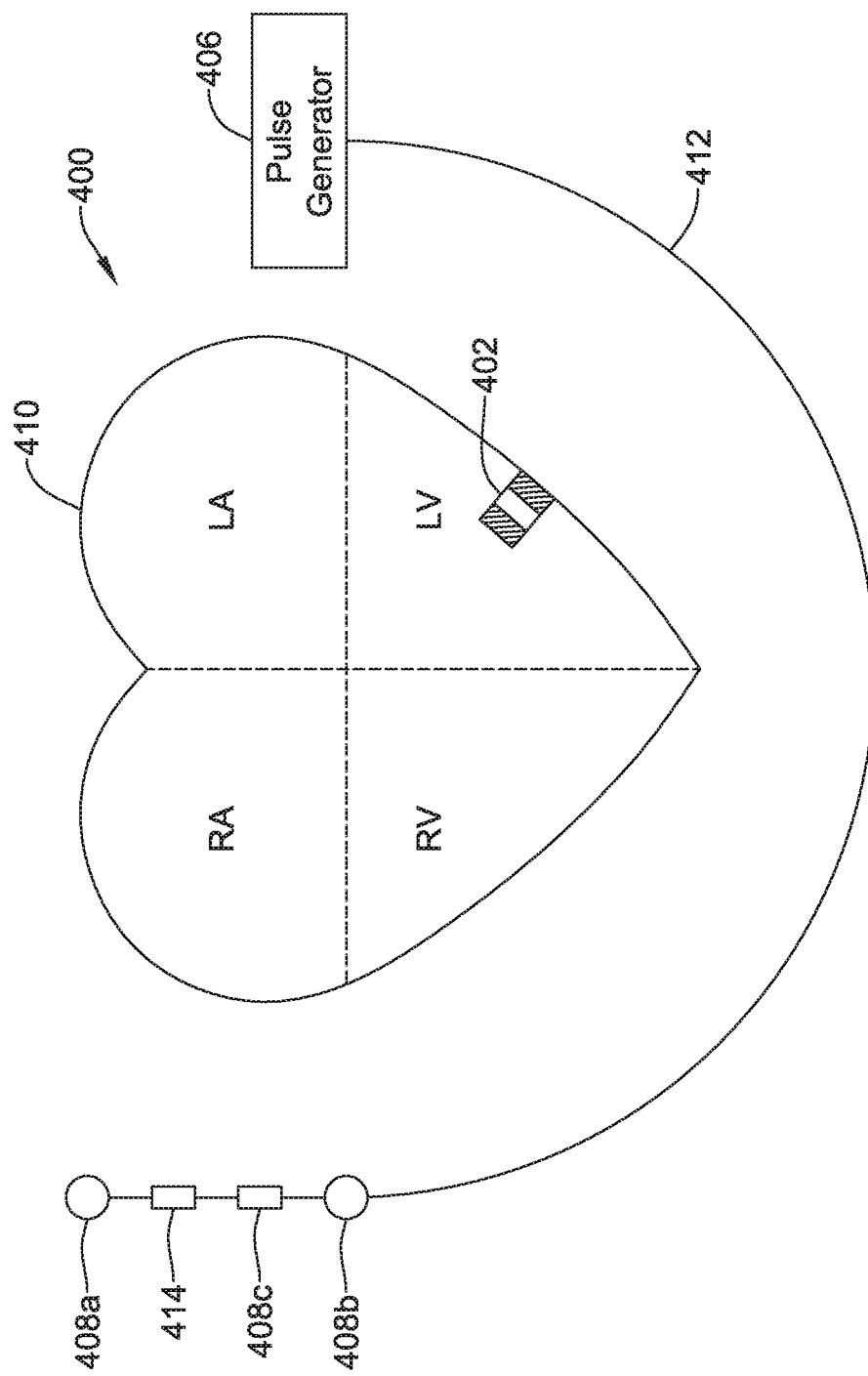
FIG. 11 is a schematic diagram of a system including an LCP and another medical device, in accordance with an example of the disclosure.

FIG. 11 shows an illustrative medical device systems. In FIG. 11, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously. In some cases, the one or more electrodes 408a-408c may be placed inside of the chest cavity but outside of the heart, such as just interior of the sternum.

In some cases, the LCP 402 may communicate with the subcutaneous implantable cardioverter-defibrillator (S-ICD). In some cases, the lead 412 may include an accelerometer 414 that may, for example, be configured to sense vibrations that may be indicative of heart sounds.

In some cases, the LCP 402 may be in the right ventricle, right atrium, left ventricle or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

When an LCP is placed in, for example, the left ventricle, and no LCP is placed in the left atrium, techniques of the present disclosure may be used to help determine an atrial contraction timing fiducial for the left atrium. This atrial contraction timing fiducial may then be used to determine a proper time to pace the left ventricle via the LCP, such as an AV delay after the atrial contraction timing fiducial.

Figure 12:
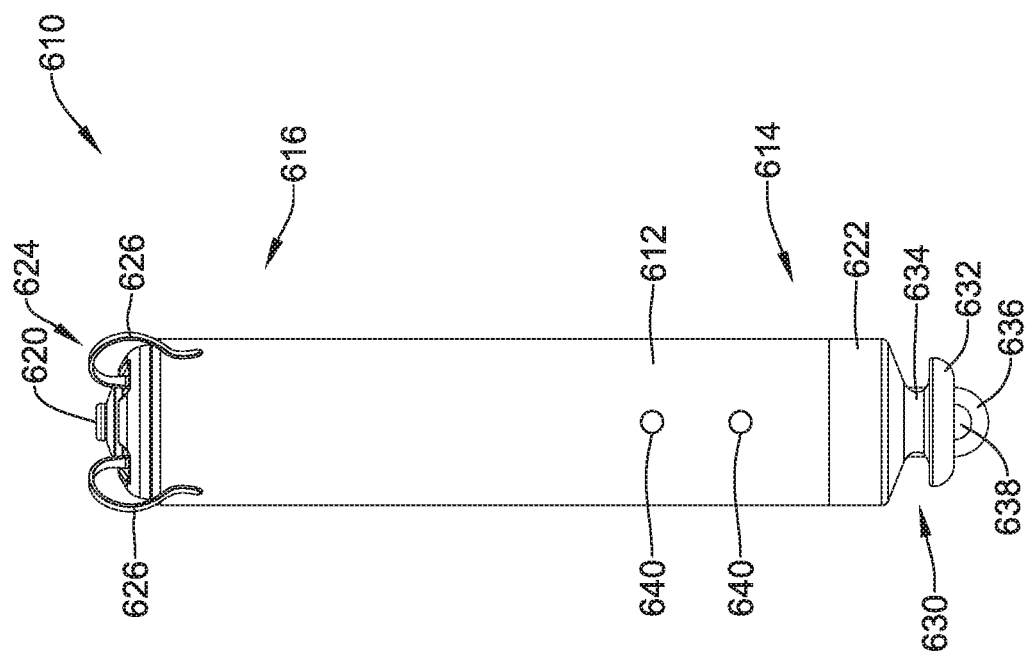
FIG. 12 is a side view of an illustrative implantable leadless cardiac device.

FIG. 12 is a side view of an illustrative implantable leadless cardiac pacemaker (LCP) 610. The LCP 610 may be similar in form and function to the LCP 100 described above. The LCP 610 may include any of the modules and/or structural features described above with respect to the LCP 100 described above. The LCP 610 may include a shell or housing 612 having a proximal end 614 and a distal end 616. The illustrative LCP 610 includes a first electrode 620 secured relative to the housing 612 and positioned adjacent to the distal end 616 of the housing 612 and a second electrode 622 secured relative to the housing 612 and positioned adjacent to the proximal end 614 of the housing 612. In some cases, the housing 612 may include a conductive material and may be insulated along a portion of its length. A section along the proximal end 614 may be free of insulation so as to define the second electrode 622. The electrodes 620, 622 may be sensing and/or pacing electrodes to provide electro-therapy and/or sensing capabilities. The first electrode 620 may be capable of being positioned against or may otherwise contact the cardiac tissue of the heart while the second electrode 622 may be spaced away from the first electrode 620. The first and/or second electrodes 620, 622 may be exposed to the environment outside the housing 612 (e.g. to blood and/or tissue).

In some cases, the LCP 610 may include a pulse generator (e.g., electrical circuitry) and a power source (e.g., a battery) within the housing 612 to provide electrical signals to the electrodes 620, 622 to control the pacing/sensing electrodes 620, 622. While not explicitly shown, the LCP 610 may also include, a communications module, an electrical sensing module, a mechanical sensing module, and/or a processing module, and the associated circuitry, similar in form and function to the modules 102, 106, 108, 110 described above. The various modules and electrical circuitry may be disposed within the housing 612. Electrical communication between the pulse generator and the electrodes 620, 622 may provide electrical stimulation to heart tissue and/or sense a physiological condition.

In the example shown, the LCP 610 includes a fixation mechanism 624 proximate the distal end 616 of the housing 612. The fixation mechanism 624 is configured to attach the LCP 610 to a wall of the heart H, or otherwise anchor the LCP 610 to the anatomy of the patient. In some instances, the fixation mechanism 624 may include one or more, or a plurality of hooks or tines 626 anchored into the cardiac tissue of the heart H to attach the LCP 610 to a tissue wall. In other instances, the fixation mechanism 624 may include one or more, or a plurality of passive tines, configured to entangle with trabeculae within the chamber of the heart H and/or a helical fixation anchor configured to be screwed into a tissue wall to anchor the LCP 610 to the heart H. These are just examples.

The LCP 610 may further include a docking member 630 proximate the proximal end 614 of the housing 612. The docking member 630 may be configured to facilitate delivery and/or retrieval of the LCP 610. For example, the docking member 630 may extend from the proximal end 614 of the housing 612 along a longitudinal axis of the housing 612. The docking member 630 may include a head portion 632 and a neck portion 634 extending between the housing 612 and the head portion 632. The head portion 632 may be an enlarged portion relative to the neck portion 634. For example, the head portion 632 may have a radial dimension from the longitudinal axis of the LCP 610 that is greater than a radial dimension of the neck portion 634 from the longitudinal axis of the LCP 610. In some cases, the docking member 630 may further include a tether retention structure 636 extending from or recessed within the head portion 632. The tether retention structure 636 may define an opening 638 configured to receive a tether or other anchoring mechanism therethrough. While the retention structure 636 is shown as having a generally "U-shaped" configuration, the retention structure 636 may take any shape that provides an enclosed perimeter surrounding the opening 638 such that a tether may be securably and releasably passed (e.g. looped) through the opening 638. In some cases, the retention structure 636 may extend though the head portion 632, along the neck portion 634, and to or into the proximal end 614 of the housing 612. The docking member 630 may be configured to facilitate delivery of the LCP 610 to the intracardiac site and/or retrieval of the LCP 610 from the intracardiac site. While this describes one example docking member 630, it is contemplated that the docking member 630, when provided, can have any suitable configuration.

It is contemplated that the LCP 610 may include one or more pressure sensors 640 coupled to or formed within the housing 612 such that the pressure sensor(s) is exposed to the environment outside the housing 612 to measure blood pressure within the heart. For example, if the LCP 610 is placed in the left ventricle, the pressure sensor(s) 640 may measure the pressure within the left ventricle. If the LCP 610 is placed in another portion of the heart (such as one of the atriums or the right ventricle), the pressures sensor(s) may measure the pressure within that portion of the heart. The pressure sensor(s) 640 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 640 may be part of a mechanical sensing module described herein. It is contemplated that the pressure measurements obtained from the pressures sensor(s) 640 may be used to generate a pressure curve over cardiac cycles. The pressure readings may be taken in combination with impedance measurements (e.g. the impedance between electrodes 620 and 622) to generate a pressure-impedance loop for one or more cardiac cycles as will be described in more detail below. The impedance may be a surrogate for chamber volume, and thus the pressure-impedance loop may be representative for a pressure-volume loop for the heart H.

In some embodiments, the LCP 610 may be configured to measure impedance between the electrodes 620, 622. More generally, the impedance may be measured between other electrode pairs, such as the additional electrodes 114' described above. In some cases, the impedance may be measure between two spaced LCP's, such as two LCP's implanted within the same chamber (e.g. LV) of the heart H, or two LCP's implanted in different chambers of the heart H (e.g. RV and LV). The processing module of the LCP 610 and/or external support devices may derive a measure of cardiac volume from intracardiac impedance measurements made between the electrodes 620, 622 (or other electrodes). Primarily due to the difference in the resistivity of blood and the resistivity of the cardiac tissue of the heart H, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 610 may be provided with energy delivery circuitry operatively coupled to the first electrode 620 and the second electrode 622 for causing a current to flow between the first electrode 620 and the second electrode 622 in order to determine the impedance between the two electrodes 620, 622 (or other electrode pair). It is contemplated that the energy delivery circuitry may also be configured to deliver pacing pulses via the first and/or second electrodes 620, 622. The LCP 610 may further include detection circuitry operatively coupled to the first electrode 620 and the second electrode 622 for detecting an electrical signal received between the first electrode 620 and the second electrode 622. In some instances, the detection circuitry may be configured to detect cardiac signals received between the first electrode 620 and the second electrode 622.

When the energy delivery circuitry delivers a current between the first electrode 620 and the second electrode 622, the detection circuitry may measure a resulting voltage between the first electrode 620 and the second electrode 622 (or between a third and fourth electrode separate from the first electrode 620 and the second electrode 622) to determine the impedance. When the energy delivery circuitry delivers a voltage between the first electrode 620 and the second electrode 622, the detection circuitry may measure a resulting current between the first electrode 620 and the second electrode 622 (or between a third and fourth electrode separate from the first electrode 620 and the second electrode 622) to determine the impedance.

In some instances, the impedance may be measured between electrodes on different devices and/or in different heart chambers. For example, impedance may be measured between a first electrode in the left ventricle and a second electrode in the right ventricle. In another example, impedance may be measured between a first electrode of a first LCP in the left ventricle and a second LCP in the left ventricle. In yet another example, impedance may be measured from an injected current. For example, a medical device (such as, but not limited to an SICD such as the SICD 12 of FIG. 1), may inject a known current into the heart and the LCP implanted in the heart H may measure a voltage resulting from the injected current to determine the impedance. These are just some examples.

Figure 13:
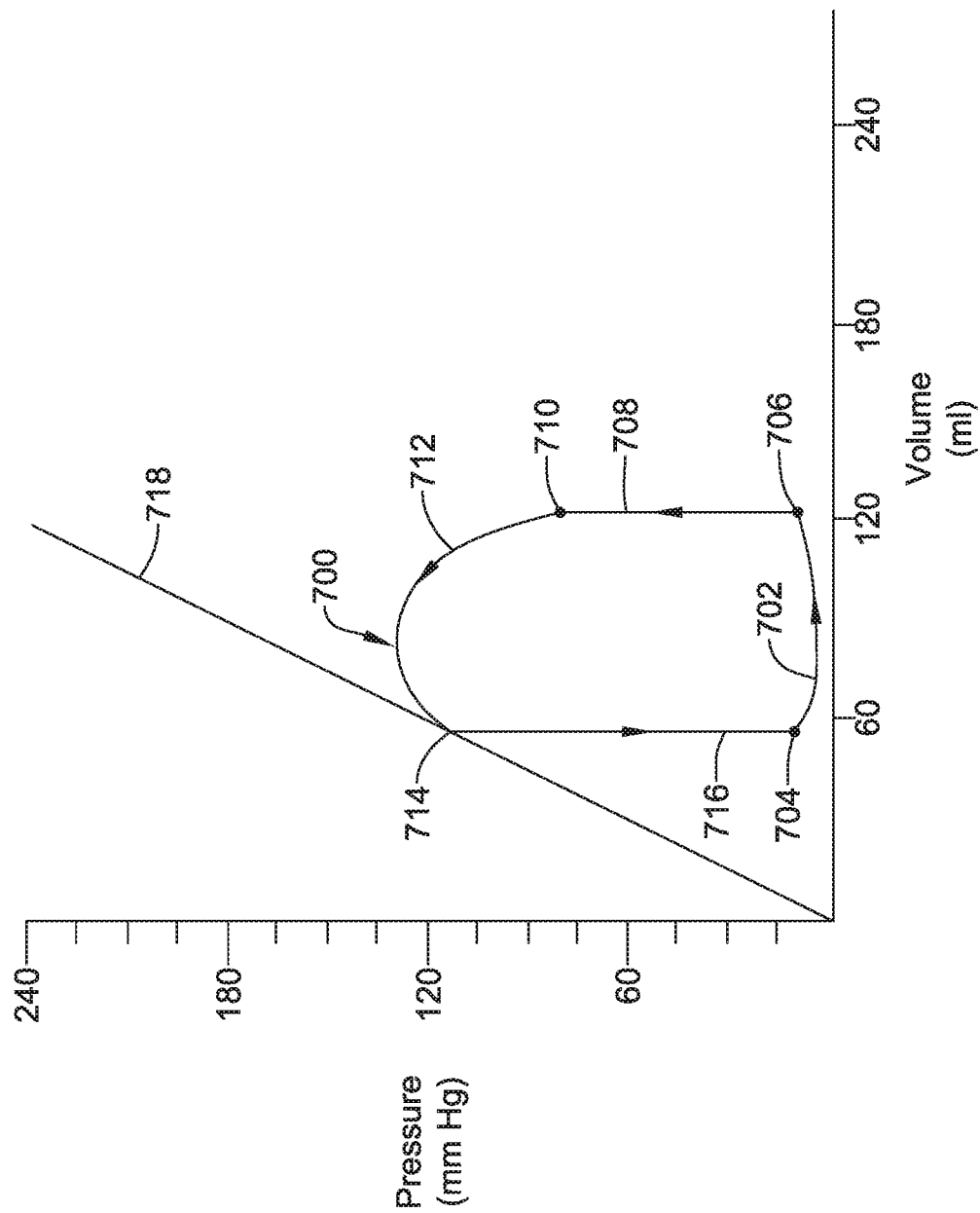
FIG. 13 is an illustrative pressure-volume loop for a ventricle of a human heart.

FIG. 13 illustrates a method of representing pressure and volume parameters of the heart in a pressure-volume (PV) loop. PV loops can be used to determine performance characteristics of the heart H. An illustrative PV loop 700 shows a normal PV characteristics for the left ventricle of the heart. The PV loop 700 moves in a counter-clockwise direction. The mitral valve opens at 704 and ventricular filling occurs along 702. Ventricular filling 702 ends at the point 706 with closure of the mitral valve. The closure of the mitral valve causes the S1 heart sound at 706. The point 706 represents the end diastolic volume (EDV) or the volume of blood in the heart at the end of its dilatation phase. The ventricle contracts at 706. Before the aortic valve opens at 710, an isovolumetric contraction phase occurs along 708 where the ventricle pressure rapidly increases but the ventricle volume does not significantly change. The ejection phase 712 lasts from point 710 until the aortic valve closes at the point 714. The closure of the aortic valve at point 714 generates the S2 heart sound, and also marks the end systolic volume (ESV), or the volume of blood in the heart at the end of its contraction phase. The isovolumetric relaxation phase 716 begins at the point 714 and continues until the mitral valve opens at point 704 and the cardiac cycle repeats. In some cases, the PV loop 700 can be approximated if the points 704, 706, 710, and 714 (the four "corners" of the PV loop) are known, for example.

The contractility index represents the capacity of the muscle to become shorter in response to a suitable stimulus. A measure of the contractility index can be estimated by calculating the slope of the end systolic pressure-volume line (shown as 718). A measure of the stroke work can be estimated by the area of the PV loop 700. A measure of the stroke volume can be estimated by the EDV minus the ESV, and represents the amount of blood ejected from the heart with each heartbeat. A measure of the ejection fraction (the proportion of the volume of blood in the ventricles at the end of diastole that is ejected during systole) can be estimated by the stroke volume divided by the EDV. These are only illustrative, and it is contemplated that other parameters may also be extracted or derived from the PV loop 700.

Figure 14:
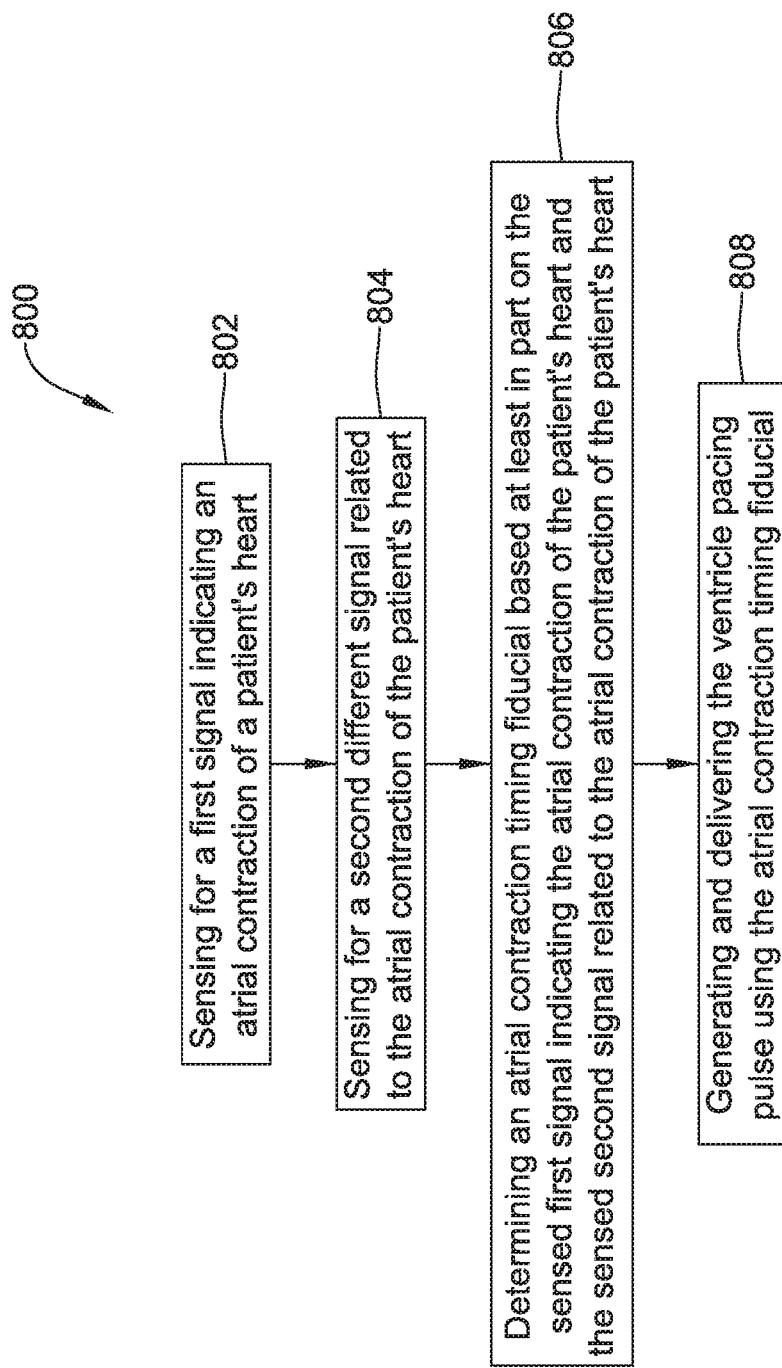
FIG. 14 is a flow diagram of an illustrative method for generating a ventricle pacing pulse.

FIG. 14 is a flow diagram showing an illustrative method 800 of generating a ventricular pulse using an LCP that is disposed with the left ventricle LV. In some cases, as indicated at block 802, a first signal indicating an atrial contraction of a patient's heart may be sensed. A second different signal related to the atrial contraction of the patient's heart may also be sensed as indicated at block 804. In some instances, the first signal and/or the second signal may be generated via a pressure sensor within the LCP. In some cases, the second signal related to the atrial contraction of the patient's heart may include an indication of a ventricular contraction of the patient's heart following the atrial contraction of the patient's heart. The controller may, as indicated at block 806, determine an atrial contraction timing fiducial based at least in part on the sensed first signal indicating the atrial contraction of the patient's heart and the sensed second signal related to the atrial contraction of the patient's heart. A ventricle pacing pulse may be generated and delivered using the atrial contraction timing fiducial, as indicated at block 808.

Figure 15:
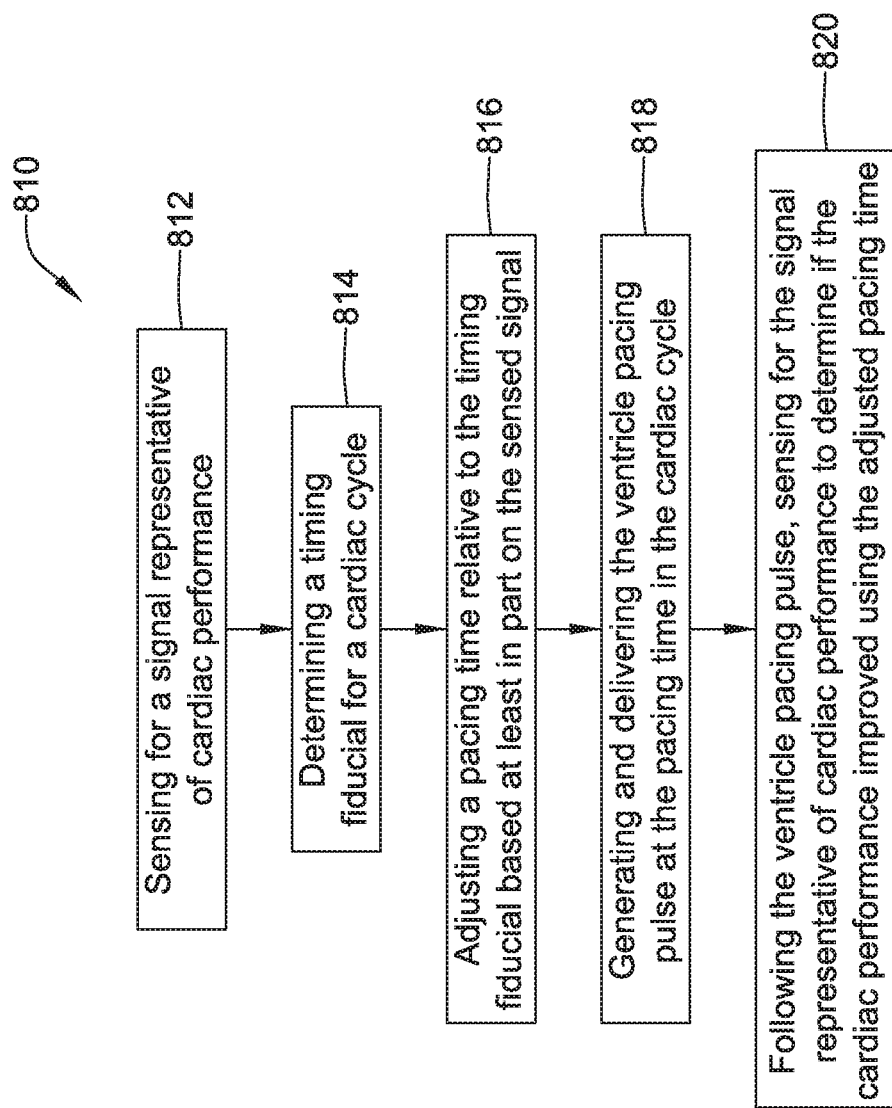
FIG. 15 is a flow diagram of an illustrative method for generating a ventricle pacing pulse.

FIG. 15 is a flow diagram showing another illustrative method 810 of generating and delivering a ventricular pulse using an LCP that is disposed with the left ventricle LV. As generally indicated at block 812, a signal representative of cardiac performance may be sensed. A timing fiducial may be determined for a cardiac cycle, as indicated at block 814. A pacing time may be adjusted relative to the timing fiducial based at least in part on the sensed signal representative of cardiac performance as indicated at block 816. As indicated at block 818, a ventricle pacing pulse may be generated and delivered at the pacing time in the cardiac cycle. Following the ventricle pacing pulse, the method 810 may include sensing for the signal representative of cardiac performance to determine if the cardiac performance improved using the adjusted pacing time, as indicated at block 820.

Figure 16:
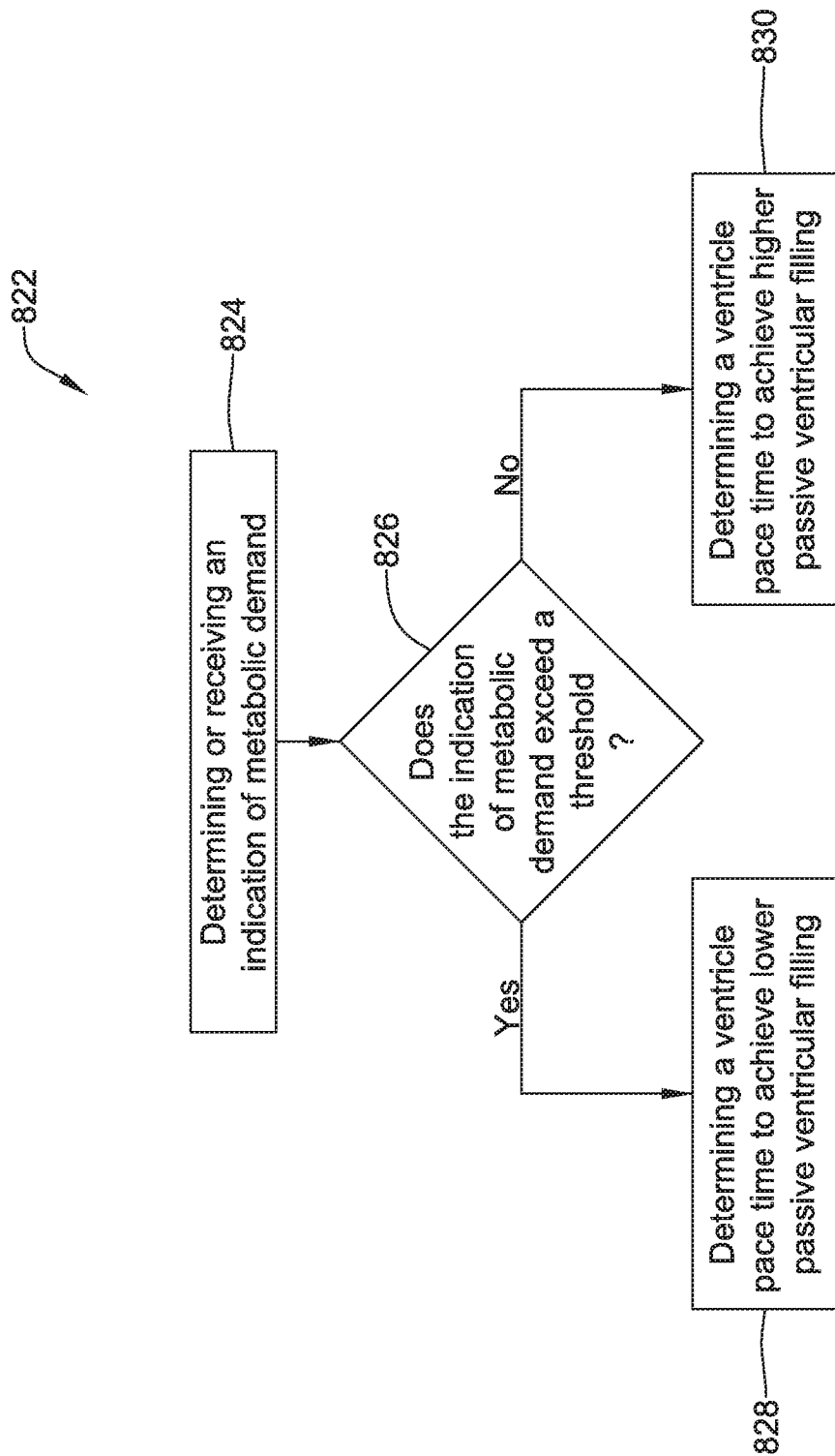
FIG. 16 is a flow diagram of an illustrative method for determining a ventricle pace time.

FIG. 16 is a flow diagram showing an illustrative method 822 of determining a ventricular pace time using an LCP that is disposed with the left ventricle LV. As seen at block 824, an indication of metabolic demand may be determined or received. At decision block 826, a determination is made as to whether the indication of metabolic demand exceeds a threshold. If yes, control passes to block 828 and a ventricle pace time may be determined to achieve lower passive ventricular filling. If not, control passes to block 830 and the ventricle pace time may be determined to achieve higher passive ventricular filling. In some cases, a measure of the passive ventricular filling is based, at least in part on, a pressure signal from a pressure sensor within the LCP.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

The invention claimed is:

1. A leadless cardiac pacemaker (LCP) configured to sense cardiac activity and to pace a patient's heart, the LCP disposable within a ventricle of the patient's heart, the LCP comprising:
   a housing;
   a first electrode secured relative to the housing;
   a second electrode secured relative to the housing, the second electrode spaced from the first electrode;
   a controller disposed within the housing and operably coupled to the first electrode and the second electrode such that the controller is capable of pacing the heart via the first electrode and the second electrode, the controller configured to receive electrical signals;
   a pressure sensor disposed relative to the housing and operably coupled to the controller, the controller configured to receive a signal from the pressure sensor, the signal from the pressure sensor including a first indication of an atrial contraction;
   an accelerometer disposed relative to the housing and operably coupled to the controller, the controller configured to receive a signal from the accelerometer, the signal from the accelerometer including a second indication of an atrial contraction;
   the controller configured to:
      establish a first confidence value for the signal from the pressure sensor and a second confidence value for the signal from the accelerometer;
      weight the signal from the pressure sensor with a first weight and weight the signal from the accelerometer with a second weight, wherein the first weight and the second weight are based at least in part upon the first confidence value and the second confidence value;
      determine an atrial contraction timing fiducial based at least in part upon the weighted signal received from the pressure sensor providing the first indication of the atrial contraction and the weighted signal received from the accelerometer providing the second indication of the atrial contraction; and
      generate a ventricle pacing pulse using the atrial contraction timing fiducial.

2. The LCP of claim 1, wherein the signal received from the pressure sensor providing the first indication of the atrial contraction comprise a pulse pressure.

3. The LCP of claim 1, wherein the received electrical signals comprises at least a portion of an electrocardiogram (ECG).

4. The LCP of claim 3, wherein the received electrical signals comprises a P-wave.

5. The LCP of claim 3, wherein another received electrical signal comprises a QRS complex, and the controller is further configured to determine a QRS width from the QRS complex.

6. The LCP of claim 3, wherein another received electrical signal comprises two consecutive R waves, and the controller is further configured to determine an R-wave to R-wave interval from the two consecutive R waves.

7. The LCP of claim 1, wherein the received electrical signals comprise electrical cardiac signals received via the first electrode and the second electrode.

8. The LCP of claim 1, wherein the received electrical signals comprise electrical signals received from an implanted medical device remote from the LCP.

9. The LCP of claim 8, wherein the implanted medical device remote from the LCP comprises an implantable cardioverter-defibrillator (ICD).

10. The LCP of claim 1, wherein the first indication of the atrial contraction comprises an A-wave.

11. The LCP of claim 1, wherein the second indication of the atrial contract comprises an S4 heart sound.

12. The LCP of claim 1, wherein the first confidence value is based at least in part upon a Signal to Noise (SNR) ratio for the signal from the pressure sensor.

13. The LCP of claim 1, wherein the second confidence value is based at least in part upon a Signal to Noise (SNR) ratio for the signal from the accelerometer.

14. The LCP of claim 1, wherein the controller is further configured to use the received electrical signals to establish a time window for looking for the first indication of the atrial contraction within the signal from the pressure sensor.

15. The LCP of claim 1, wherein the controller is further configured to use the received electrical signals to establish a time window for looking for the second indication of the atrial contraction within the signal from the accelerometer.

16. A leadless cardiac pacemaker (LCP) configured to sense cardiac activity and to pace a patient's heart, the LCP disposable within a ventricle of the patient's heart, the LCP comprising:

a housing;

a first electrode secured relative to the housing;

a second electrode secured relative to the housing, the second electrode spaced from the first electrode;

a controller disposed within the housing and operably coupled to the first electrode and the second electrode such that the controller is capable of receiving, via the first electrode and the second electrode, electrical signals from a remotely implanted medical device;

a pressure sensor disposed relative to the housing and operably coupled to the controller, the controller configured to receive a signal from the pressure sensor, the signal from the pressure sensor including a first indication of an atrial contraction;

an accelerometer disposed relative to the housing and operably coupled to the controller, the controller configured to receive a signal from the accelerometer, the signal from the accelerometer including a second indication of an atrial contraction;

the controller configured to:
  establish a first confidence value for the signal from the pressure sensor and a second confidence value for the signal from the accelerometer;
  weight the signal from the pressure sensor with a first weight and weight the signal from the accelerometer with a second weight, wherein the first weight and the second weight are based at least in part upon the first confidence value and the second confidence value;
  determine an atrial contraction timing fiducial based at least in part upon the weighted signal received from the pressure sensor providing the first indication of the atrial contraction, the weighted a signal received from the accelerometer providing the second indication of the atrial contraction, and the electrical signals received from the remotely located implanted medical device; and
  generate a ventricle pacing pulse using the atrial contraction timing fiducial.

* * * * *